(12) United States Patent
Bianchi et al.

(10) Patent No.: US 7,273,498 B2
(45) Date of Patent: *Sep. 25, 2007

(54) OPEN INTERVERTEBRAL SPACER

(75) Inventors: John R. Bianchi, Gainesville, FL (US);
Kevin C. Carter, Gainesville, FL (US);
Bradley T. Estes, Memphis, TN (US);
Larry Boyd, Memphis, TN (US); John A. Pafford, Germantown, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 409 days.

This patent is subject to a terminal disclaimer.

(21) Appl. No.: 10/756,971

(22) Filed: Jan. 13, 2004

(65) Prior Publication Data
US 2004/0148029 A1 Jul. 29, 2004

Related U.S. Application Data

(60) Continuation of application No. 10/035,074, filed on Dec. 28, 2001, now Pat. No. 6,695,882, which is a continuation of application No. 09/453,787, filed on Dec. 3, 1999, now Pat. No. 6,409,765, which is a division of application No. 08/867,963, filed on Jun. 3, 1997, now Pat. No. 6,033,438.

(51) Int. Cl.
*A61F 2/44* (2006.01)
(52) U.S. Cl. .................................................. 623/17.16
(58) Field of Classification Search ... 623/17.11–17.16

See application file for complete search history.

(56) References Cited

U.S. PATENT DOCUMENTS 3,486,505 A 12/1969 Morrison
(Continued)

FOREIGN PATENT DOCUMENTS

DE 37 41 493 A1 6/1989
(Continued)

OTHER PUBLICATIONS

*Bone Graft Surgery in Disease, Injury and Deformity*; Fred H. Albee, M.D.; Published by D. Appleton-Century Company, Copyright 1940.
(Continued)

Primary Examiner—Suzette Gherbi
(74) Attorney, Agent, or Firm—Krieg DeVault LLP

(57) ABSTRACT

Open chambered spacers, implanting tools and methods are provided. The spacers 500' include a body 505' having a wall 506' which defines a chamber 530' and an opening 531' in communication with the chamber 530'. In one embodiment the wall 506' includes a pair of arms 520', 521' facing one another and forming a mouth 525' to the chamber 530'. Preferably, one of the arms 520' is truncated relative to the other, forming a channel 526. In one aspect the body 505' is a bone dowel comprising an off-center plug from the diaphysis of a long bone. The tools 800 include spacer engaging means for engaging a spacer and occlusion means for blocking an opening defined in the spacer. In some embodiments, the occlusion means 820 includes a plate 821 extendable from the housing 805. In one specific embodiment the plate 821 defines a groove 822 which is disposed around a fastener 830 attached to the housing 805 so that the plate 821 is slideable relative to the housing 805.

46 Claims, 21 Drawing Sheets

U.S. PATENT DOCUMENTS

| | | |
|---|---|---|
| 3,848,601 A | 11/1974 | Ma |
| 4,309,488 A | 1/1982 | Heide et al. |
| 4,545,374 A | 10/1985 | Jacobson |
| 4,626,392 A | 12/1986 | Kondo et al. |
| 4,636,217 A | 1/1987 | Ogilvie et al. |
| 4,654,314 A | 3/1987 | Takagi et al. |
| 4,687,675 A | 8/1987 | Nakano et al. |
| 4,714,469 A | 12/1987 | Kenna |
| 4,722,870 A | 2/1988 | White |
| 4,736,738 A | 4/1988 | Lipovsek et al. |
| 4,743,256 A | 5/1988 | Brantigan |
| 4,820,305 A | 4/1989 | Harms et al. |
| 4,834,757 A | 5/1989 | Brantigan |
| 4,877,020 A | 10/1989 | Vich |
| 4,878,915 A | 11/1989 | Brantigan |
| 4,904,261 A * | 2/1990 | Dove et al. ............. 623/17.16 |
| 4,917,703 A | 4/1990 | Albrektsson |
| 4,950,296 A | 8/1990 | McIntyre |
| 4,961,740 A | 10/1990 | Ray et al. |
| 4,976,738 A | 12/1990 | Frey et al. |
| 5,002,583 A | 3/1991 | Pitaru et al. |
| 5,015,247 A | 5/1991 | Michelson |
| 5,026,373 A | 6/1991 | Ray et al. |
| 5,055,104 A | 10/1991 | Ray |
| 5,062,845 A | 11/1991 | Kuslich |
| 5,190,548 A | 3/1993 | Davis |
| 5,250,061 A | 10/1993 | Michelson |
| 5,258,029 A | 11/1993 | Chu et al. |
| 5,282,861 A | 2/1994 | Kaplan |
| 5,306,302 A | 4/1994 | Bauer et al. |
| 5,306,303 A | 4/1994 | Lynch |
| 5,306,309 A | 4/1994 | Wagner et al. |
| 5,329,846 A | 7/1994 | Bonutti |
| 5,330,826 A | 7/1994 | Taylor et al. |
| 5,346,492 A | 9/1994 | Morgan |
| 5,423,825 A | 6/1995 | Levine |
| 5,423,855 A | 6/1995 | Marienne |
| 5,425,772 A | 6/1995 | Brantigan |
| 5,443,514 A | 8/1995 | Steffee |
| 5,445,639 A | 8/1995 | Kuslich et al. |
| 5,458,638 A | 10/1995 | Kuslich et al. |
| 5,458,642 A | 10/1995 | Beer et al. |
| 5,484,437 A | 1/1996 | Michelson |
| 5,489,307 A | 2/1996 | Kuslich et al. |
| 5,489,308 A | 2/1996 | Kuslich et al. |
| 5,499,984 A | 3/1996 | Steiner |
| 5,514,180 A | 5/1996 | Heggeness et al. |
| 5,591,235 A | 1/1997 | Kuslich |
| 5,593,409 A | 1/1997 | Michelson |
| 5,609,636 A | 3/1997 | Kohrs et al. |
| 5,645,598 A | 7/1997 | Brosnahan, III |
| 5,669,909 A | 9/1997 | Zdeblick et al. |
| 5,709,683 A | 1/1998 | Bagby |
| 5,716,355 A | 2/1998 | Jackson et al. |
| 5,720,749 A | 2/1998 | Rupp |
| 5,728,159 A | 3/1998 | Stoever et al. |
| 5,741,253 A | 4/1998 | Michelson |
| 5,766,253 A | 6/1998 | Brosnahan, III |
| 5,782,830 A | 7/1998 | Farris |
| 5,810,819 A | 9/1998 | Errico et al. |
| 5,814,084 A | 9/1998 | Grivas et al. |
| 5,857,995 A | 1/1999 | Thomas et al. |
| 5,904,719 A | 5/1999 | Errico et al. |
| 5,972,368 A | 10/1999 | McKay |
| 5,989,289 A | 11/1999 | Coates |
| 6,017,343 A | 1/2000 | Rogozinski |
| 6,033,438 A | 3/2000 | Bianchi et al. |
| 6,096,081 A | 8/2000 | Grivas |
| 6,111,164 A | 8/2000 | Rainey et al. |
| 6,120,506 A | 9/2000 | Kohrs et al. |
| 6,258,125 B1 | 7/2001 | Paul et al. |
| 6,371,988 B1 * | 4/2002 | Pafford et al. ........... 623/17.11 |
| 6,375,681 B1 | 4/2002 | Truscott |
| 6,391,058 B1 | 5/2002 | Kuslich et al. |
| 6,409,765 B1 | 6/2002 | Bianchi et al. |
| 6,500,206 B1 | 12/2002 | Bryan |

FOREIGN PATENT DOCUMENTS

| | | |
|---|---|---|
| EP | 0 077 159 A | 4/1983 |
| EP | 0 307 241 | 3/1989 |
| EP | 0 392 076 | 10/1990 |
| GB | 2 207 607 A | 2/1989 |
| WO | WO 95/08306 | 3/1995 |
| WO | WO 95/15133 | 6/1995 |
| WO | WO 96/22747 | 8/1996 |
| WO | WO 96/40013 | 12/1996 |
| WO | WO 97/13378 | 4/1997 |
| WO | WO 97/15248 | 5/1997 |
| WO | WO 97/25945 | 7/1997 |
| WO | WO 98/17209 | 4/1998 |
| WO | WO 98/17330 | 4/1998 |
| WO | WO 01/70144 | 9/2001 |

OTHER PUBLICATIONS

"Laparoscopic Bone Dowel Surgical Technique", Sofamor Danek, Memphis, Tennessee, 1995.
"Muskuloskeletal Transplant Foundation" Brochure, Apr. 1996.
"Threaded Bone Dowel" by LISpine 1997 Hohmann Enterprises Inc., Apr. 1997.
"New and Innovative Fusion Techniques" by John J. Vaughan, MD The Kentucky Spines Inst., Dec. 1998.
AcroMed Spine Tools, *PLIG Instruments* (undated).
AcroMed, *Brantigan I/F Cage*, (undated).
AcroMed, *Brantigan I/F Cage™ for PLIF* (1991).
Sofamor Danek, *Surgical Technique Using Bone Dowel Instrumentation for Posterior Approach*, LIT.PLIF.ST96 (1996).
Sofamor Danek, *Surgical Tips Posterior Approach* (1998).
University of Florida Tissue Bank, Inc. *Allograft Catalog* (1998).

* cited by examiner

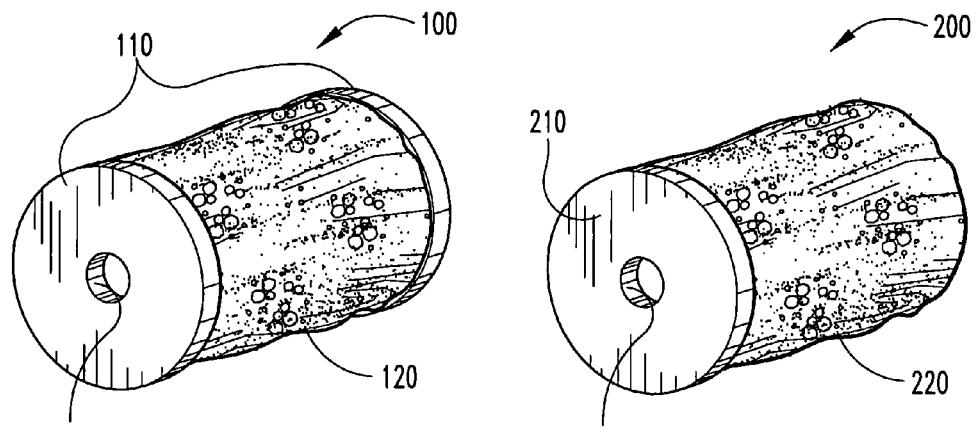
Fig. 1
(Prior Art)
Fig. 2
(Prior Art)
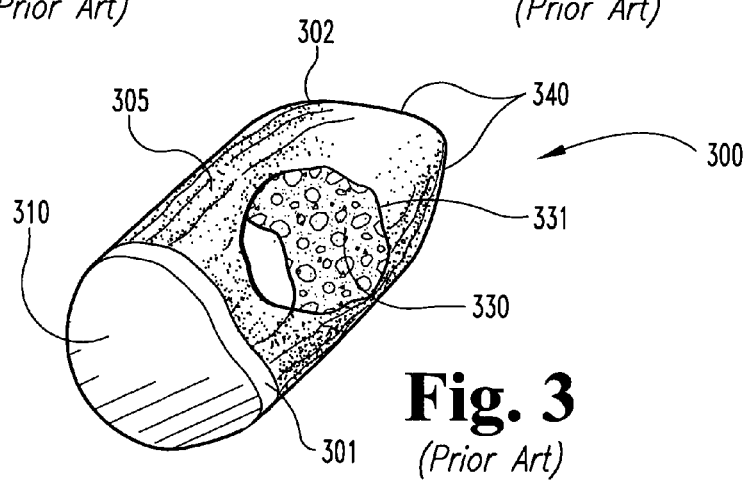
Fig. 3
(Prior Art)
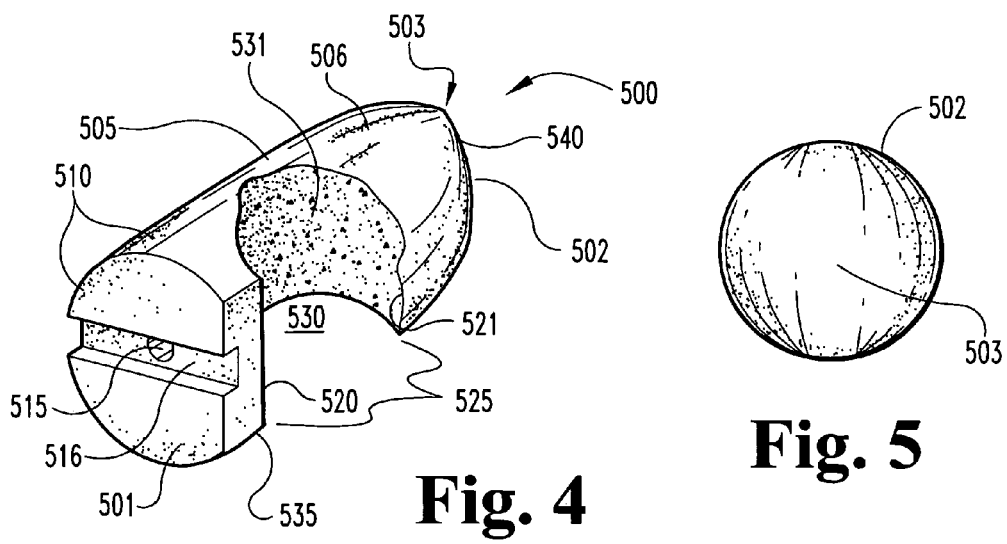
Fig. 4
Fig. 5

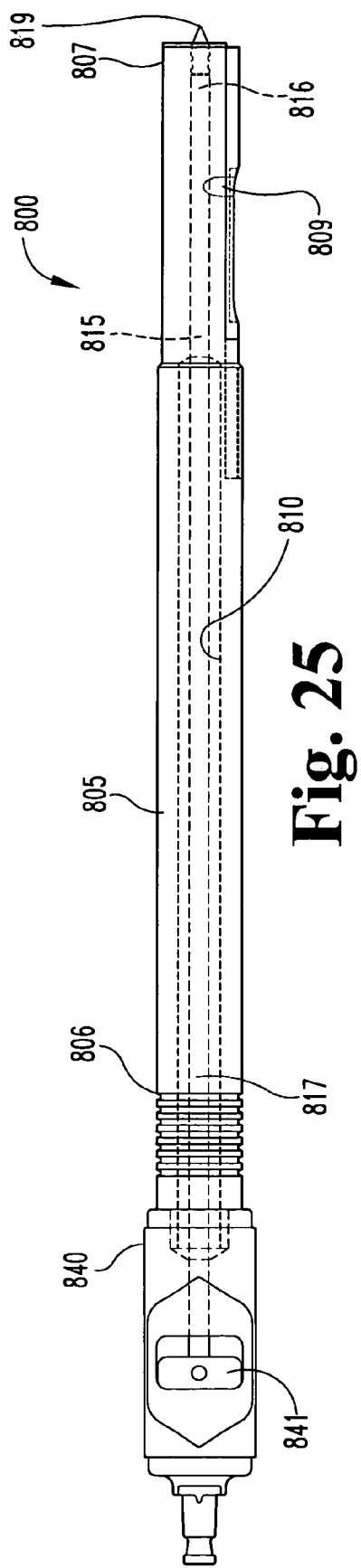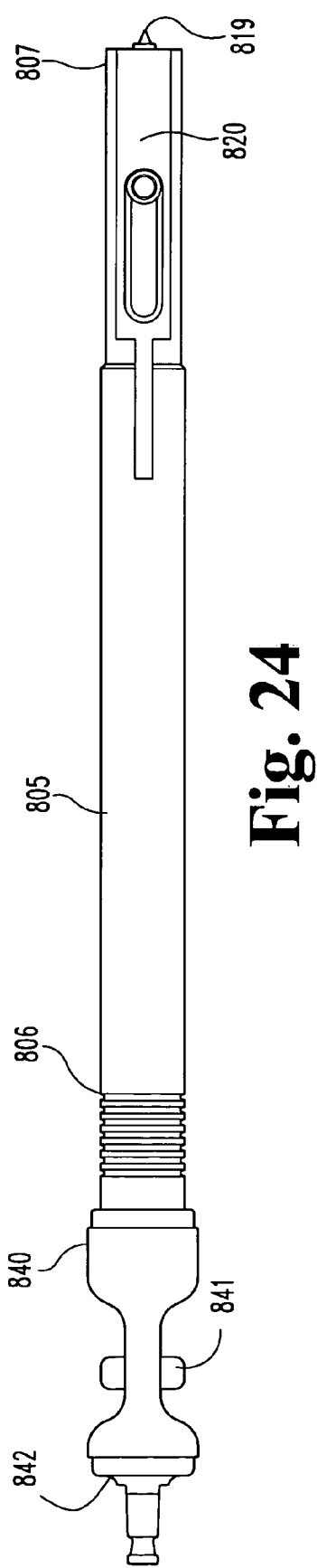

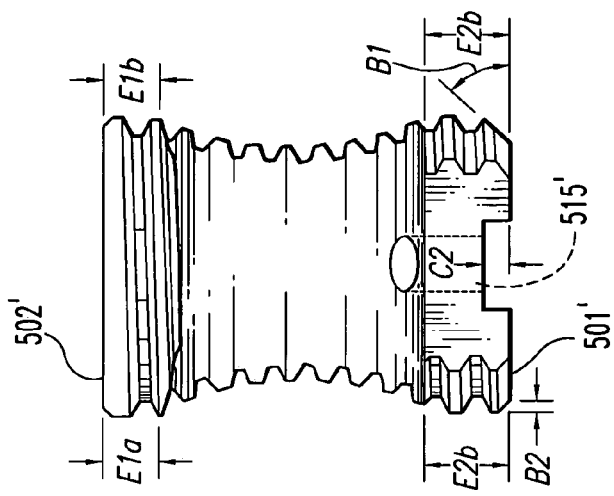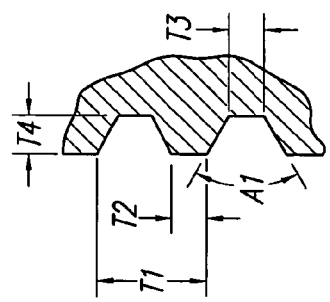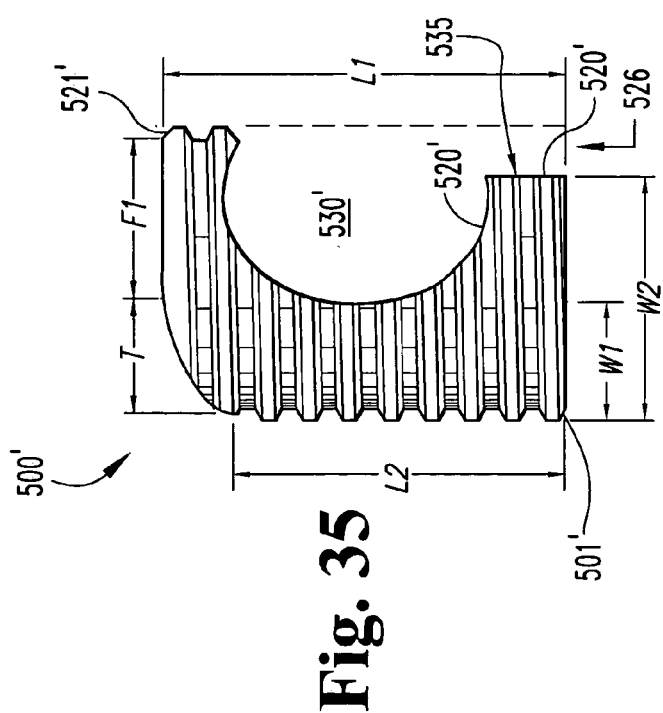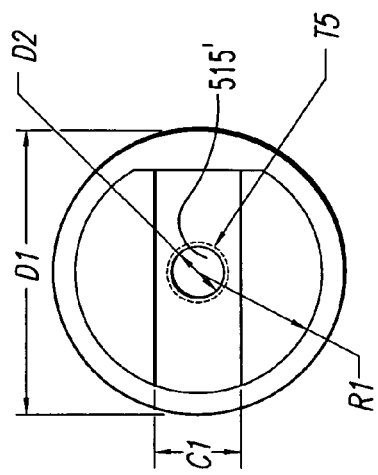
Fig. 36
Fig. 38
Fig. 35
Fig. 37

OPEN INTERVERTEBRAL SPACER

CROSS REFERENCE TO RELATED APPLICATIONS

This application is a continuation of U.S. patent application Ser. No. 10/035,074, now U.S. Pat. No. 6,695,882. filed on Dec. 28, 2001, which is a continuation of U.S. patent application Ser. No. 09/453,787, now U.S. Pat. No. 6,409,765, filed on Dec. 3,1999, which is a divisional of U.S. patent application Ser. No. 08/867,963, now U.S. Pat. No. 6,033,438, filed on Jun. 3, 1997, all of which are incorporated herein by reference in their entirety.

FIELD OF THE INVENTION

The present invention broadly concerns arthrodesis for stabilizing the spine. More specifically, the invention provides open-chambered intervertebral spacers, instruments for implanting the spacers and methods for making and using the spacers.

BACKGROUND OF THE INVENTION

Intervertebral discs, located between the endplates of adjacent vertebrae, stabilize the spine, distribute forces between vertebrae and cushion vertebral bodies. A normal intervertebral disc includes a semi-gelatinous component, the nucleus pulposus, which is surrounded and confined by an outer, fibrous ring called the annulus fibrosus. In a healthy, undamaged spine, the annulus fibrosus prevents the nucleus pulposus from protruding outside the disc space.

Spinal discs may be displaced or damaged due to trauma, disease or aging. Disruption of the annulus fibrosus allows the nucleus pulposus to protrude into the vertebral canal, a condition commonly referred to as a herniated or ruptured disc. The extruded nucleus pulposus may press on a spinal nerve, which may result in nerve damage, pain, numbness, muscle weakness and paralysis. Intervertebral discs may also deteriorate due to the normal aging process or disease. As a disc dehydrates and hardens, the disc space height will be reduced leading to instability of the spine, decreased mobility and pain.

Sometimes the only relief from the symptoms of these conditions is a discectomy, or surgical removal of a portion or all of an intervertebral disc followed by fusion of the adjacent vertebrae. The removal of the damaged or unhealthy disc will allow the disc space to collapse. Collapse of the disc space can cause instability of the spine, abnormal joint mechanics, premature development of arthritis or nerve damage, in addition to severe pain. Pain relief via discectomy and arthrodesis requires preservation of the disc space and eventual fusion of the affected motion segments.

Bone grafts are often used to fill the intervertebral space to prevent disc space collapse and promote fusion of the adjacent vertebrae across the disc space. In early techniques, bone material was simply disposed between the adjacent vertebrae, typically at the posterior aspect of the vertebra, and the spinal column was stabilized by way of a plate or rod spanning the affected vertebrae. Once fusion occurred, the hardware used to maintain the stability of the segment became superfluous and was a permanent foreign body. Moreover, the surgical procedures necessary to implant a rod or plate to stabilize the level during fusion were frequently lengthy and involved.

It was therefore determined that a more optimal solution to the stabilization of an excised disc space is to fuse the vertebrae between their respective end plates, preferably without the need for anterior or posterior plating. There have been an extensive number of attempts to develop an acceptable intradiscal implant that could be used to replace a damaged disc and maintain the stability of the disc interspace between the adjacent vertebrae, at least until complete arthrodesis is achieved. The implant must provide temporary support and allow bone ingrowth. Success of the discectomy and fusion procedure requires the development of a contiguous growth of bone to create a solid mass because the implant may not withstand the compressive loads on the spine for the life of the patient.

Several metal spacers have been developed to fill the void formed and to promote fusion. Sofamor Danek Group, Inc., (1800 Pyramid Place, Memphis, Tenn. 38132, (800) 933-2635) markets a number of hollow spinal cages. For example, U.S. Pat. No. 5,015,247 to Michelson and U.S. Ser. No. 08/411,017 to Zdeblick disclose a threaded spinal cage. The cages are hollow and can be filled with osteogenic material, such as autograft or allograft, prior to insertion into the intervertebral space. Apertures defined in the cage communicate with the hollow interior to provide a path for tissue growth between the vertebral endplates.

Although the metal fusion devices of Sofamor Danek and others are widely and successfully employed for reliable fusions, it is sometimes desirable to use an all-bone product. Bone-provides many advantages for use in fusions. It can be incorporated after fusion occurs and therefore will not be a permanent implant. Bone allows excellent postoperative imaging because it does not cause scattering like metallic implants. Stress shielding is avoided because bone grafts have a similar modulus of elasticity as the surrounding bone. Although an all-bone spacer provides these and other benefits, the use of bone presents several challenges. Any spacer which will be placed within the intervertebral disc space must withstand the cyclic loads of the spine. Cortical bone products may have sufficient compressive strength for such use, however, cortical bone will not promote rapid fusion. Cancellous bone is more conducive to fusion but is not biomechanically sound as an intervertebral spacer.

Several bone dowel products such as the Cloward Dowel have been developed over the years. Bone dowels in the shape of a generally circular pin can be obtained by drilling an allogeneic or autogeneic plug from bone. As shown in FIGS. 1 and 2, the dowels 100, 200 have one or two cortical surfaces 110 and an open, latticed body of brittle cancellous bone 120, 220 backing the cortical surface 210 or between the two cortical surfaces 110. The dowels 100, 200 also include a drilled and/or tapped instrument attachment hole 115, 215. Dowels and other bone products are available from the University of Florida Tissue Bank, Inc., (1 Innovation Drive, Alachua, Fla. 32615, 904-462-3097 or 1-800-OA-GRAFT; Product numbers 280012, 280014, and 280015).

While the bone dowels of the prior art are valuable bone grafting materials, these dowels have relatively poor biomechanical properties, in particular a low compressive strength. Accordingly, these dowels may not be suitable as an intervertebral spacer without internal fixation due to the risk of collapsing prior to fusion under the intense cyclic loads of the spine. A need remains for dowels having the advantages of allograft but with even greater biomechanical strength.

In response to this need, the University of Florida Tissue Bank, Inc., has developed a proprietary bone dowel machined from the diaphysis of long bones. Referring now to FIG. 3, the dowel 300 includes a tool engagement end 301 and an opposite insertion end 302. Between the two ends 301 and 302, the dowel 300 includes a chamber 330 formed from the naturally occurring medullary canal of the long bone and an opening 331 in communication with the chamber 330. The chamber 330 can be packed with an osteogenic material to promote fusion while the cortical body 305 of the dowel 300 provides support. The dowels are also advantageous in that they provide desirable biomechanics and can be machined for various surface features such as threads or annular ribbing. In some embodiments, the outer cortical surface 310 of the tool engagement end 301 is machined with an instrument attachment feature and an alignment score mark. As shown in FIG. 3, the insertion end 302 may include a chamfered portion 340.

While these diaphysial cortical dowels are a major advance in this field, a need has remained for bone dowels and other intervertebral spacers with greater versatility.

SUMMARY OF THE INVENTION

This invention provides spacers having an open chamber, tools for implanting the spacers and methods for making and using the spacers. The spacers include a body having a wall which defines a chamber and an opening in communication with the chamber. In one aspect, a channel is defined in the wall in communication with the chamber and the outer surface of the spacer. In another embodiment the wall includes a pair of arms facing one another and forming a mouth to the chamber. In a preferred embodiment, one of the arms is truncated relative to the other. In some aspects, the body is composed of bone. In one aspect the body is a dowel having a substantially C-shaped chamber and comprising an off-center bone plug obtained from the diaphysis of a long bone.

Tools for implanting spacers are also provided. The tools include spacer engaging means for engaging a spacer and occlusion means for blocking an opening defined in the spacer. In one aspect the engaging means includes a shaft slidingly disposed within a housing and having a threaded post for engaging a threaded tool hole in the spacer. In some embodiments, the occlusion means includes a plate extendable from the housing. In one specific embodiment the plate defines a groove which is disposed around a fastener attached to the housing so that the plate is slideable relative to the housing.

This invention also includes methods for obtaining an open bone dowel and methods for using the spacers of this invention. The methods of making a dowel according to this invention include cutting an off-center plug from the diaphysis of a long bone to obtain a bone dowel having an open chamber. In one aspect, the dowel is machined to include desirable surface features such as threads, grooves and instrument holes. In still another aspect, the methods include chamfering the forward end of the dowel. The methods for using the spacers of this invention include making a cavity between two vertebrae to be fused and implanting a spacer having an open chamber. In some embodiments the chamber is packed with osteogenic material before the spacer is implanted. In other aspects of the invention, osteogenic material is packed into and around the chamber through the mouth or channel after implantation.

The combination of the open-chambered spacers of this invention with the tools and methods of this invention provide a versatile spacer without any compromise in biomechanical integrity. The spacers can be packed before or after implantation. This invention facilitates implanting a pair of open spacers close to each other in an intervertebral space. Where the spacer is a bone dowel, the dowel can be formed with less bone than is needed for conventional dowels, conserving precious bone stock.

Accordingly, it is one object of this invention to provide an open-chambered fusion spacer and methods for using the spacer in an arthrodesis procedure.

Another object is to improve patient incidence of safe and satisfactory spinal stabilization and fusion.

Another object of this invention is to provide a dowel for vertebra fusions which has improved biomechanical properties and versatility over standard dowels known in the art.

Still another object of the present invention is to provide a spacer with satisfactory biomechanical features and improved osteogenic and fusion promoting features.

These and other objects, advantages and features are accomplished according to the spacers, tools and methods of the following description of the preferred embodiments of the present invention.

BRIEF DESCRIPTION OF THE DRAWINGS

FIG. 1 shows a standard Cloward Dowel known in the art.

FIG. 2 shows a standard unicortical dowel known in the art.

FIG. 3 shows a diaphysial cortical dowel produced and sold by The University of Florida Tissue Bank, Inc.

FIG. 4 is a side perspective view of one embodiment of the open-chambered spacer of this invention.

FIG. 5 is an end elevational view of the spacer of FIG. 4.

FIG. 24 is a top perspective view of one embodiment of an insertion tool of this invention.

FIG. 25 is a side perspective view of the tool of FIG. 24.

FIG. 35 is a top elevational view of a spacer according to one specific embodiment of this invention.

FIG. 36 is a side view of the spacer of FIG. 35.

FIG. 37 is a front perspective view of the spacer of FIG. 35.

FIG. 38 is a detail of a portion of the threaded surface of the spacer of FIG. 35.

DESCRIPTION OF THE PREFERRED EMBODIMENTS

Figure 6:
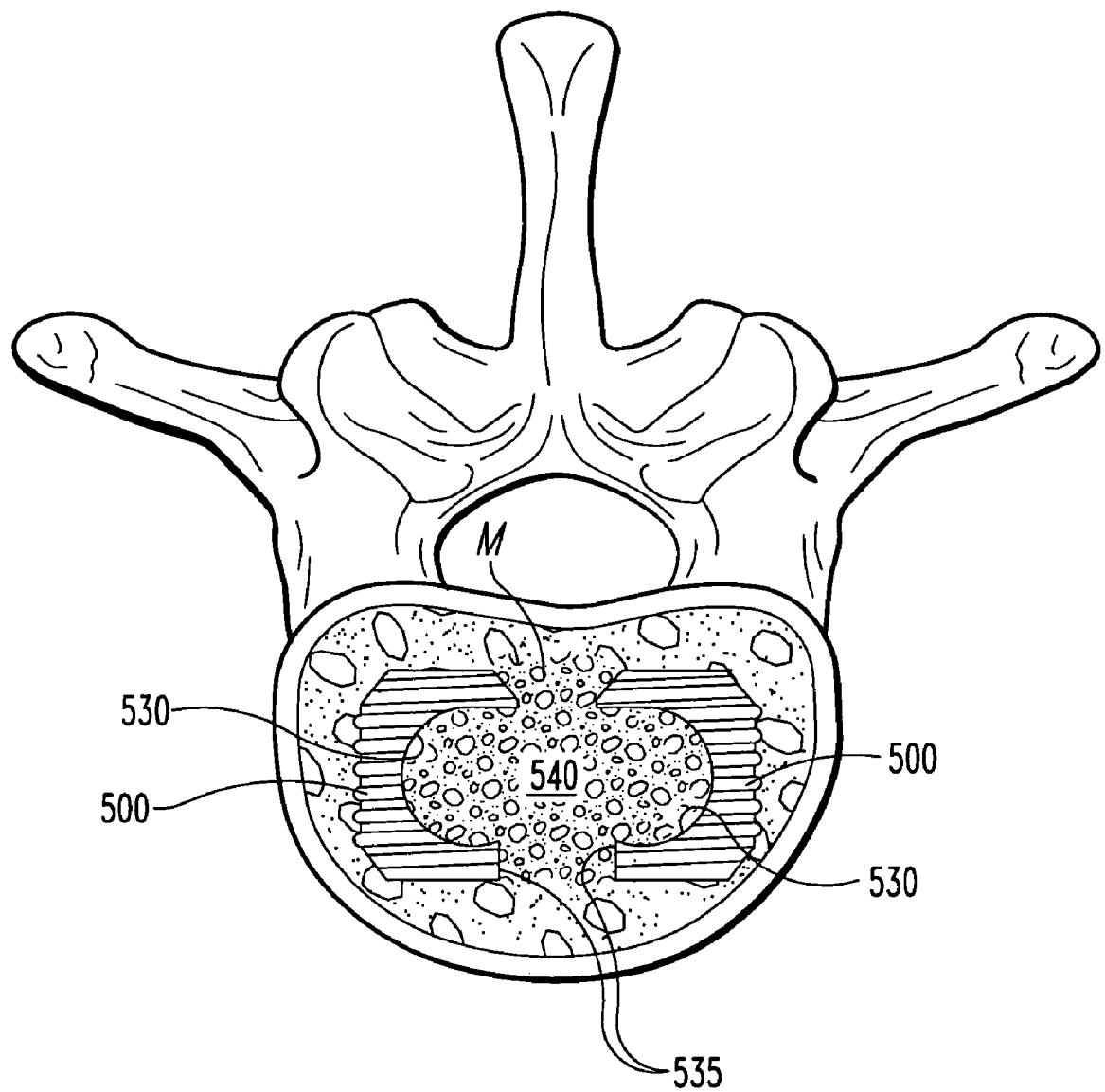
FIG. 6 is a top elevational view of a pair of open chambered dowels of this invention implanted within an intervertebral space.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

This invention provides spacers having an open-mouthed chamber. These spacers are advantageous for maximum exposure of vertebral tissue to osteogenic material within the chamber and allow close placement of a pair of spacers within the intervertebral space. The design of these spacers conserve material without compromising biomechanical properties of the spacer. This is particularly advantageous when the material is bone because the invention preserves precious allograft. In fact, larger dowels and other shaped grafts can be obtained from smaller bones than was ever thought possible before the present invention. Likewise, smaller dowels having a pre-formed chamber may be efficiently obtained from larger bones.

Although any open-chambered spacer is contemplated, in one embodiment the spacers are obtained as an off-center transverse plug from the diaphysis of a long bone. This results in a dowel having an open-mouthed chamber. Because the long bone naturally includes the medullary canal, a pre-formed chamber is inherently contained within the dowel. When the plug is cut off-center in a certain way, the dowel includes an open-mouthed chamber. Surprisingly, the biomechanical properties of these dowels are not compromised by the absence of the missing chamber wall.

Referring now to FIGS. 4 and 5, one embodiment of an interbody fusion spacer of this invention is shown. The spacer 500 includes a body 505 with a tool engagement end 501 and an opposite insertion end 502. The body 505 includes a wall 506 defining a chamber 530 between the two ends 501, 502 and an opening 531 in communication with the chamber 530. Preferably, the insertion end 502 includes a solid protective wall 503 which is positionable to protect the spinal cord from escape or leakage of osteogenic material from the chamber 530 when the spacer is placed via an anterior approach.

As shown in FIG. 4, the chamber 530 is open in that it also communicates with a further aperture such as a mouth or a channel. The aperture also communicates with the outer surface 510 of the spacer 500, preferably at the tool engagement end 501. The aperture can provide access to the chamber 530 after implantation or can facilitate insertion of the spacer 530 into the intervertebral space. Comparing FIG. 4 with FIG. 3, it is evident that the chamber 530 is open so that the body 505 and chamber 530 are substantially C-shaped as opposed to the defined chamber 330 of FIG. 3. In some embodiments, including the one depicted in FIG. 4, the aperture is a mouth 525 formed by a pair of facing and opposing arms 520, 521.

Bilateral placement of dowels 500 is preferred as shown in FIG. 6. This configuration provides a substantial quantity of bone graft available for the fusion. The dual bilateral cortical dowels 500 result in a significant area of cortical bone for load bearing and long-term incorporation via creeping substitution, while giving substantial area for placement of osteogenic autogenous bone which will facilitate boney bridging across the disc space. The dual dowel placement with facing chambers 530 results in an elongated compartment 540 that can be filled with an osteogenic composition M. This provides for the placement of a significant amount of osteogenic material as well as a large support area of cortical bone for load bearing.

Figure 7:
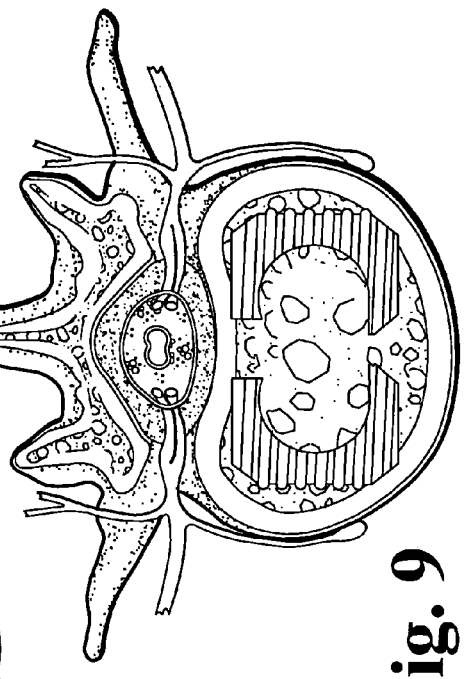
FIG. 7 depicts the anatomy of a lumbar vertebral segment.
Figure 8:
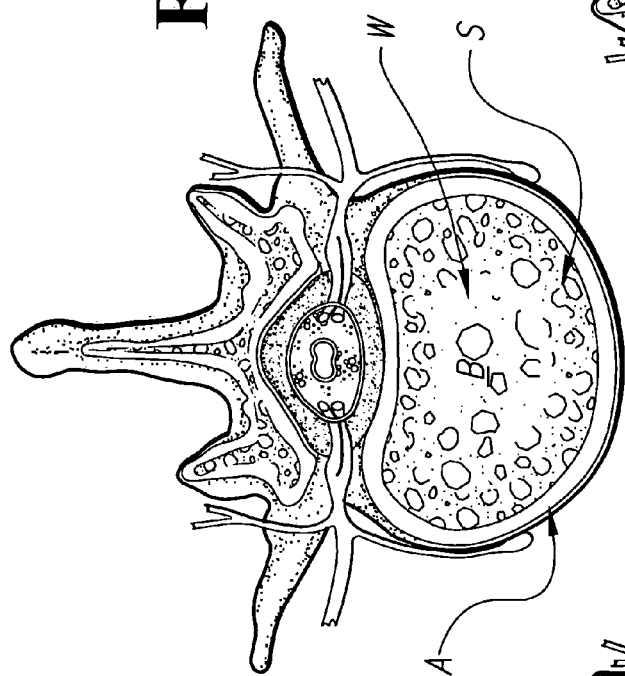
FIG. 8 is a top elevational view of a pair of open chambered dowels of this invention implanted within an intervertebral space via an anterior surgical approach.
Figure 9:
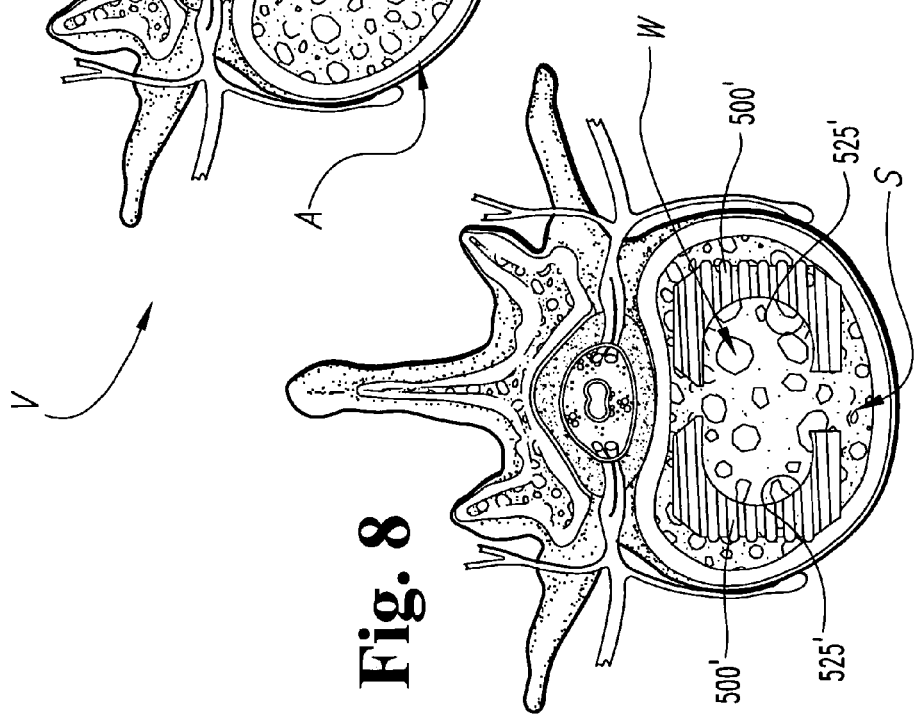
FIG. 9 is a top elevational view of a pair of open chambered dowels of this invention implanted within an intervertebral space via a posterior surgical approach.

The open spacers of this invention are advantageous because they complement the anatomy of the vertebrae V as shown in FIGS. 7-9. FIG. 7 shows the variation in bone strength within the vertebral body V, with weaker bone W, disposed toward the center of the body B, and stronger bone S being disposed around the periphery, closest to the ring apophysis A. The open spacers of this invention are designed to accommodate spinal anatomy. As shown in FIG. 8, two open spacers 500' can be implanted with the mouths 525' facing to the center of the intervertebral space. This capitalizes on the load bearing capability of the stronger peripheral bone S of the vertebral body V by placing the structural and load bearing portion of the spacer along the periphery of the body. At the same time, the osteogenic material M placed within the chambers is exposed to the more vascular center area W of the body.

Figure 10:
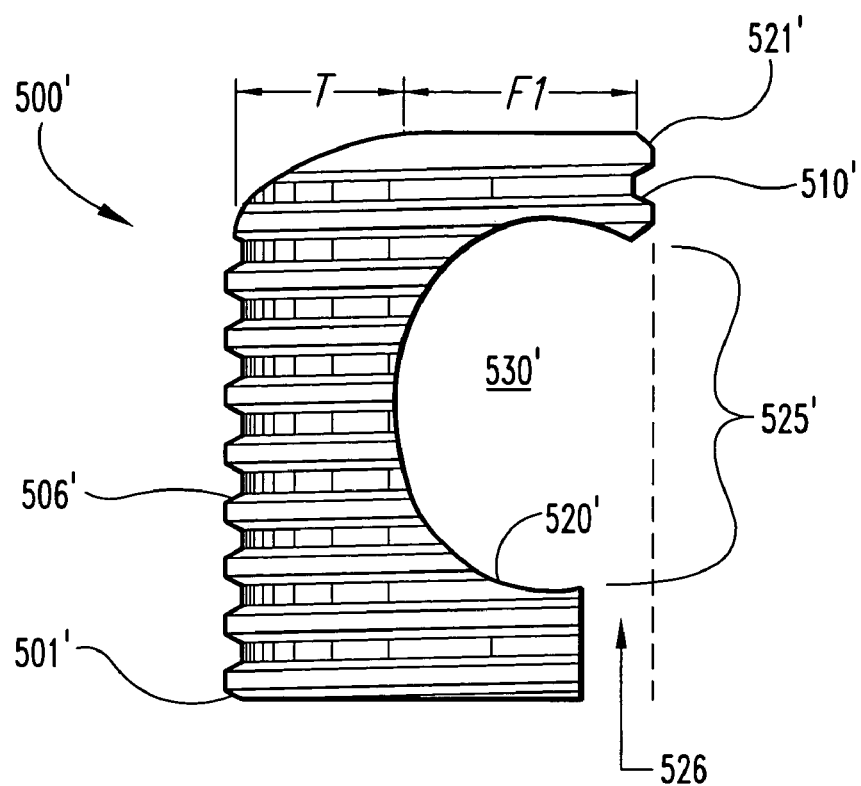
FIG. 10 is a side perspective view of one embodiment of an open chambered dowel having a truncated arm defining a channel to the mouth and chamber.
Figure 11:
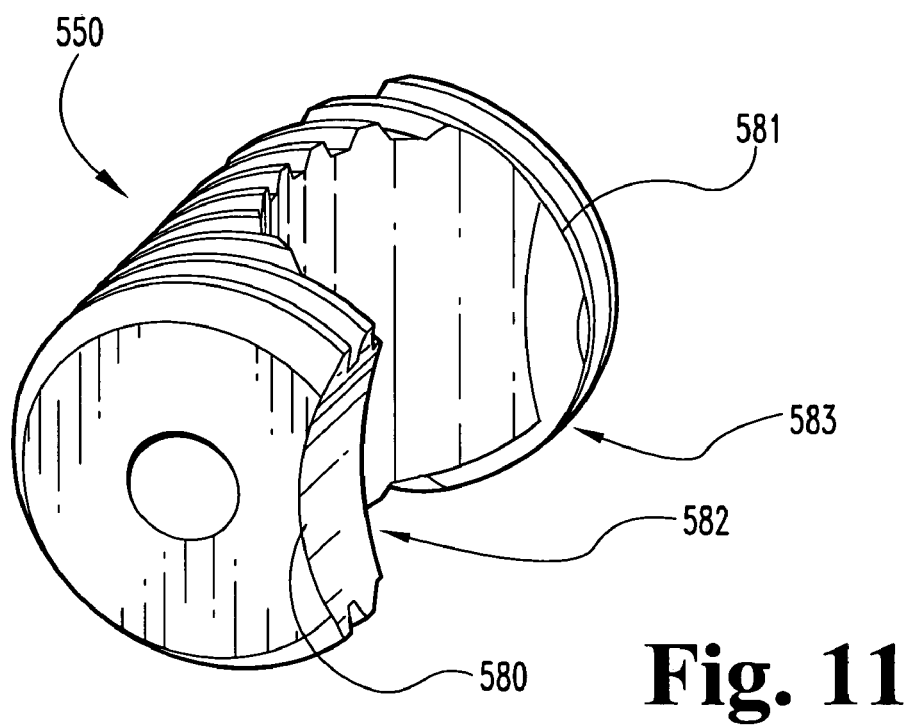
FIG. 11 is a top perspective view of an open chambered dowel with arms defining concave faces.

In a preferred embodiment shown in FIG. 10, the first arm 520' or the arm adjacent the tool engagement end 501', is truncated relative to the second arm 521'. This forms a channel 526 from the outer surface 510' to the chamber 530'. Preferably and as shown in FIG. 10, the channel 526' is in communication with both the mouth 525' and the chamber 530' although it is contemplated that the channel 526 could be provided in a closed spacer having a chamber and an opening. In some embodiments, such as the spacer 550 depicted in FIG. 11, the arms 580, 581 define concave faces or surfaces 582 and 583. The concave faces 582 and 583 are configured to receive a complementary driving tool.

The channel 526 of this invention provides important advantages. The channel 526, particularly when formed as a truncated arm 520' as shown in FIG. 10, facilitates implantation with an insertion tool. Because the tool can be placed within the channel during implantation, two spacers of this invention can be placed very closely together within the intervertebral space as shown in FIGS. 6 and 8. The tool need not extend beyond the outer surface of the spacer. The channel 526 also allows osteogenic material to be packed within the chamber and around the spacer after implantation. A further advantage of the channel is that, when it is formed in combination with the mouth of an open spacer, it allows the chamber of the spacer to be packed before implantation. The tool may be placed within the channel to prevent escape of the osteogenic material from the chamber during implantation. The channel 526 also provides access to the chamber 530' for packing after the spacer 500' is implanted into the disc space.

Figure 12:
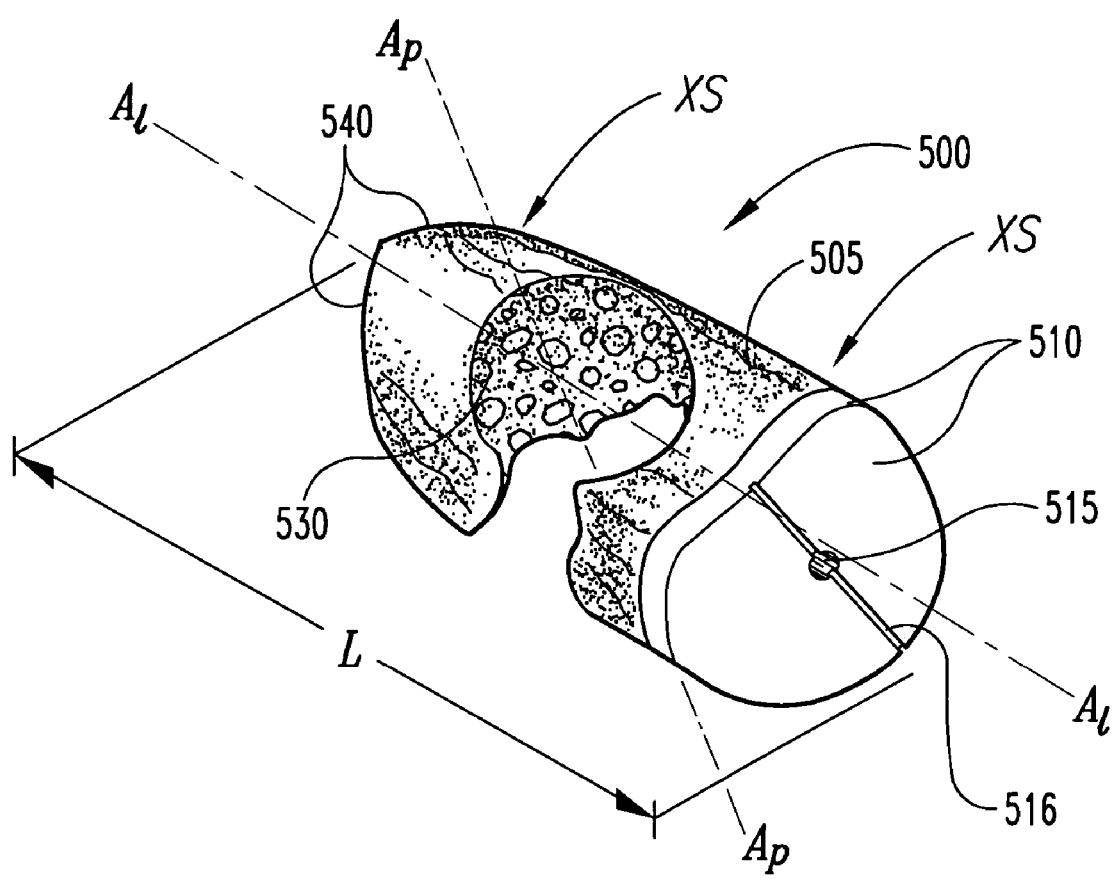
FIG. 12 is a top perspective view of an open chambered bone dowel.

Referring now to FIG. 12, in a preferred embodiment, the spacer is a dowel having a longitudinal axis $A_1$ along a length L of the body 505. The open C-shaped chamber 530 is defined along a second axis $A_p$ substantially perpendicular to the longitudinal axis $A_1$. The body 505 has an outer cross-section XS projected on a plane perpendicular to the longitudinal axis $A_1$ that is substantially uniform along the length L of the body 505.

The spacers of this invention may be provided with surface features defined in the outer surface 510. Where the spacer is a bone dowel as described herein, the surface features can be machined into the cortical bone. Any desirable surface feature is contemplated. In one embodiment the outer surface 510 of the tool engaging end 501 defines a tool engaging or instrument attachment hole 515 as shown in FIGS. 4 and 12. In a preferred embodiment, the hole 515 is threaded but any suitable configuration is contemplated. It is sometimes preferable that this end 501 have a generally flat surface to accept the instrument for insertion of the dowel in the recipient.

In some embodiments, the spacer 500 includes an alignment score mark or groove 516 defined in the tool engagement end 501. In FIG. 12 the groove 516 is parallel to the axis $A_p$ of the chamber 530 or perpendicular as shown in FIG. 4. The score mark may be widened to form a driver slot for receiving an implantation tool. Alternatively, the end of the dowel may be machined to exhibit a projection instead of a slot. Such a protruding portion of bone may take a straight, flat-sided shape (essentially a mirror image of the slot shown), it may be an elliptical eminence, a bi-concave eminence, a square eminence, or any other protruding shape which provides sufficient end-cap or tool engaging end strength and drive purchase to allow transmission of insertional torque without breaking the dowel or the eminence. In other embodiments, a groove can be omitted to enhance the strength of the tool engaging end 501.

Figure 13:
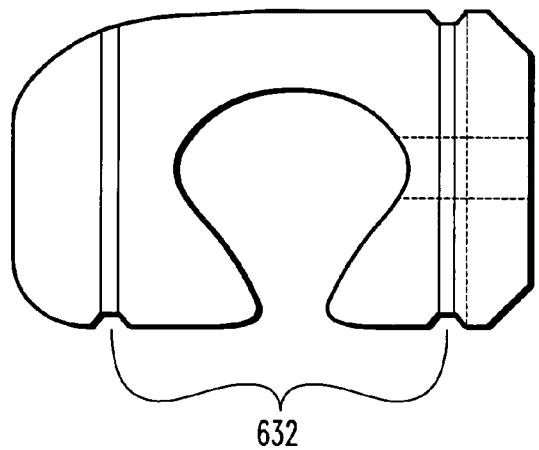
FIG. 13 is a side perspective view of one embodiment of this invention in which the dowel is grooved.
Figure 14:
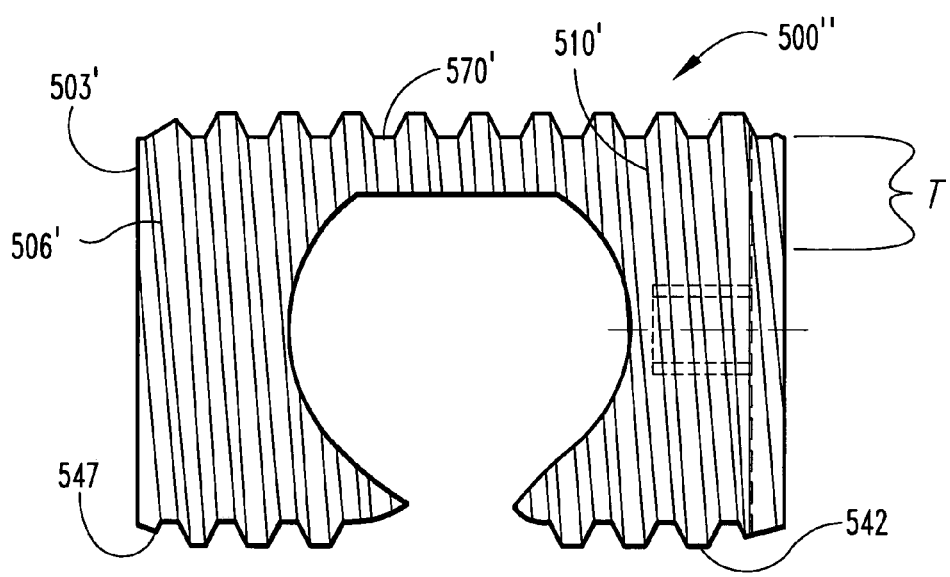
FIG. 14 is a side perspective view of a threaded dowel of this invention.
Figure 15:
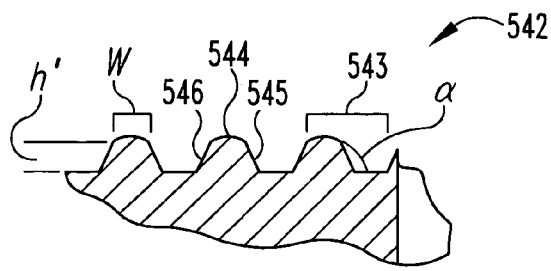
FIG. 15 is a side cross-sectional view of a detail of a portion of the threads of a spacer of this invention.

Other surface features can be defined along the length L of the spacer. The surface features can provide engaging surfaces to facilitate engagement with the vertebrae and prevent slippage of the spacer as is sometimes seen with a smooth graft. Referring now to FIG. 13, the spacer 600 includes a groove or stop rib 632 inscribed along the circumference of the spacer. The rib 632 discourages backing out. In other preferred embodiments the outer surface 510' of the dowel 500" defines threads 542 as shown in FIG. 14. The initial or starter thread 547 is adjacent the protective wall 503'. As shown more clearly in FIG. 15, the threads 542 are preferably uniformly machined threads which include teeth 543 having a crest 544 between a leading flank 545 and an opposite trailing flank 546. Preferably the crest 544 of each tooth 543 is flat. In one specific embodiment, the crest 544 of each tooth 543 has a width w of between about 0.020 inches and about 0.030 inches. The threads 542 preferably define an angle α between the leading flank 545 and the trailing flank 546 of adjacent ones of said teeth 543. The angle α is preferably between about 50 degrees and 70 degrees. Each tooth 543 preferably has a height h' which is about 0.030 inches and about 0.045 inches.

Machined surfaces, such as threads, provide several advantages that were previously only available with metal implants. Threads allow better control of spacer insertion than can be obtained with a smooth surface. This allows the surgeon to more accurately position the spacer and avoid over-insertion which is extremely important around the critical neurological and vascular structures of the spinal column. Threads and the like also provide increased surface area which facilitates the process of bone healing and creeping substitution for replacement of the donor bone material and fusion. These features also increase postoperative stability of the spacer by engaging the adjacent vertebral endplates and anchoring the spacer to prevent expulsion. Surface features also stabilize the bone-spacer interface and reduce micromotion to facilitate incorporation and fusion.

Figure 16A:
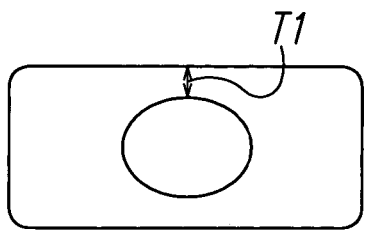
FIG. 16 shows various cuts across bone diaphysis and the resulting dowels formed according to this invention.
Figure 16B:
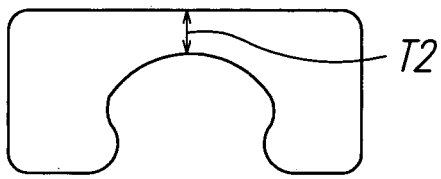
Figure 16C:
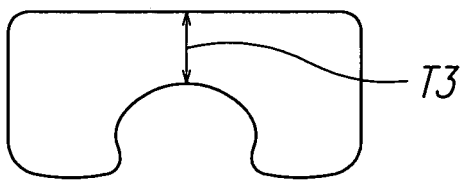
Figure 16D:
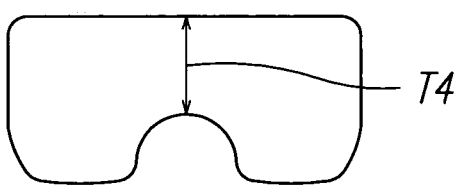
Figure 16:
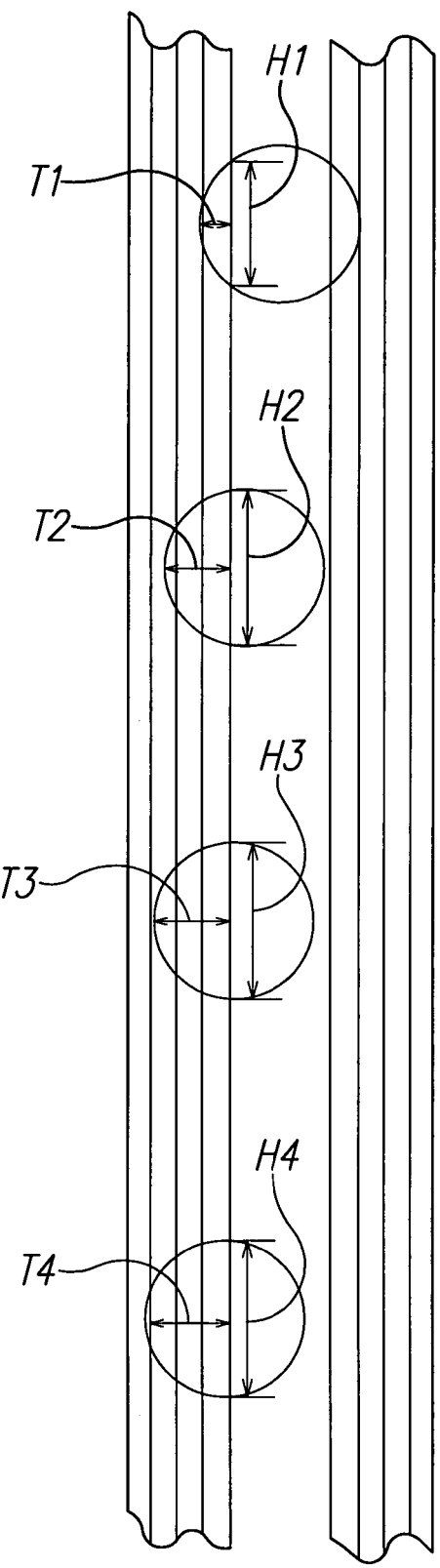
Figure 17:
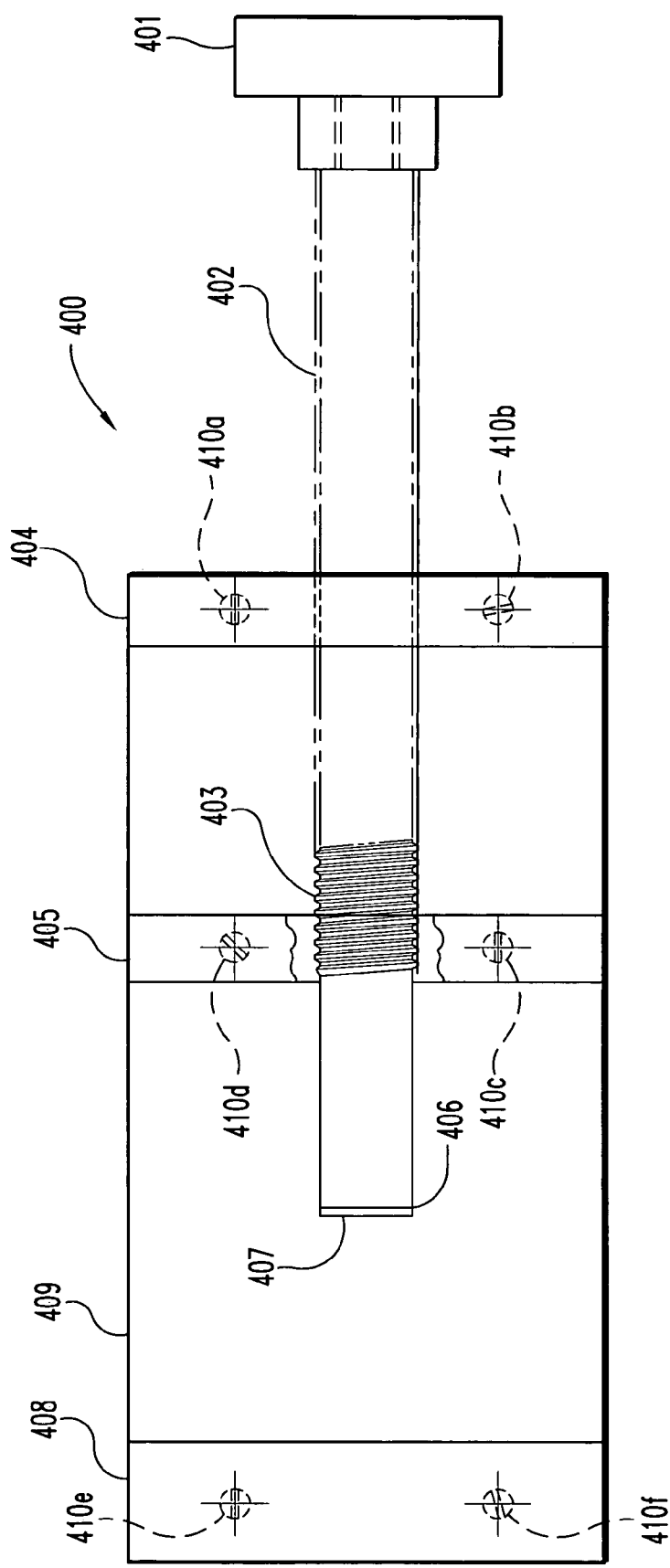
FIG. 17 is a top elevational view of one embodiment of a dowel threader of this invention.

Various configurations of open-chambered spacers are contemplated by this invention. When the spacer is obtained from the diaphysis of a long bone, the shape of the dowel is determined by the location of the cut into the bone shaft. Referring now to FIG. 16, by appropriately locating the plug that is cut, "C"-shaped dowels of varying "C"-shaped cavity depths and sidewall thicknesses are achievable. FIG. 16A shows the plug that must be cut into the shaft to obtain a diaphysial cortical dowel 300 (see FIG. 3) having a sidewall height H1 and a sidewall thickness T1. FIGS. 16B-16D depict the off-center cuts required to generate "C"-shaped dowels of this invention having different sidewall heights H2-H4 and sidewall thicknesses T2-T4. The sidewall thickness increases from 16A to 16D, even though the diameter of the dowel is unchanged.

Surprisingly, we have found that the open chambered spacers of this invention have biomechanical properties similar to a spacer having a defined or closed chamber. For example, the open-chambered bone dowel 500", of FIG. 14 is no more susceptible to snapping or breakage during machining or implantation than the diaphysial cortical dowel 300 of FIG. 3 having a full circular chamber. This strength is retained as long as the thickness T4 of the wall 506' at its narrowest aspect 570 is preferably no less than about 5 mm.

As any of these open-chambered spacers are implanted and begin to experience axial load, it is expected that the lower the sidewall height H, the greater the load carried by the dowel end 501, 502. However, where the sidewall height H is approximately the same as the dowel diameter D, the sidewall 506 may carry a greater share of this axial load.

In some embodiments, the wall 506 may include upper and lower flattened portions to stabilize the dowel by neutralizing any rotational torque that may be induced by pressure on the sidewall. This could be achieved by reducing the height H of the sidewall 505 and ends 501, 502 by filing or like means. These considerations may be less important for a threaded dowel than a non-threaded dowel as the threads tend to "bite" into the bone in which they are implanted, thereby preventing any rotation.

For cervical fusions, the dowel is preferably obtained from the fibula, radius, ulna or humerus. The dimensions of such dowels are typically between about 8-15 mm in length or depth and about 10-14 mm in diameter. For thoracic and lumbar fusions, the dowel is preferably obtained from the humerus, femur or tibia. The dimensions of such dowels are typically between about 10-30 mm in length and about 14-20 mm in diameter.

The chamber may be packed with any suitable osteogenic material. In a preferred embodiment, the osteogenic composition M has a length which is greater than the length of the chamber 530 so that the osteogenic composition will contact the endplates of the adjacent vertebrae when the spacer 500 is implanted within the vertebrae. This provides better contact of the composition with the endplates to stimulate bone ingrowth.

Any suitable osteogenic material or composition is contemplated, including autograft, allograft, xenograft, demineralized bone, synthetic and natural bone graft substitutes, such as bioceramics and polymers, and osteoinductive factors. The terms osteogenic material or osteogenic composition used here means virtually any material that promotes bone growth or healing including autograft, allograft, zenograft, bone graft substitutes and natural, synthetic and recombinant proteins, hormones and the like.

Autograft can be harvested from locations such as the iliac crest using drills, gouges, curettes and trephines and other tools and methods which are well known to surgeons in this field. Preferably, autograft is harvested from the iliac crest with a minimally invasive donor surgery. The osteogenic material may also include bone reamed away by the surgeon while preparing the end plates for the spacer.

Advantageously, where autograft is chosen as the osteogenic material, only a very small amount of bone material is needed to pack the chamber. The autograft itself is not required to provide structural support as this is provided by the spacer. The donor surgery for such a small amount of bone is less invasive and better tolerated by the patient. There is usually little need for muscle dissection in obtaining such small amounts of bone. The present invention therefore eliminates or minimizes many of the disadvantages of employing autograft.

Natural and synthetic graft substitutes which replace the structure or function of bone are also contemplated for the osteogenic composition. Any such graft substitute is contemplated, including for example, demineralized bone matrix, mineral compositions and bioceramics. As is evident from a review of An Introduction to Bioceramics, edited by Larry L. Hench and June Wilson (World Scientific Publishing Co. Ptd. Ltd, 1993, volume 1), there is a vast array of bioceramic materials, including BIOGLASS®, hydroxyapatite and calcium phosphate compositions known in the art which can be used to advantage for this purpose. That disclosure is herein incorporated by reference for this purpose. Preferred calcium compositions include bioactive glasses, tricalcium phosphates and hydroxyapatites. In one embodiment, the graft substitute is a biphasic calcium phosphate ceramic including tricalcium phosphate and hydroxyapatite.

In some embodiments, the osteogenic compositions used in this invention comprise a therapeutically effective amount to stimulate or induce bone growth of a substantially pure bone inductive or growth factor or protein in a pharmaceutically acceptable carrier. The preferred osteoinductive factors are the recombinant human bone morphogenetic proteins (rhBMPs) because they are available in unlimited supply and do not transmit infectious diseases. Most preferably, the bone morphogenetic protein is a rhBMP-2, rhBMP-4 or heterodimers thereof.

Recombinant BMP-2 can be used at a concentration of about 0.4 mg/ml to about 1.5 mg/ml, preferably near 1.5 mg/ml. However, any bone morphogenetic protein is contemplated including bone morphogenetic proteins designated as BMP-1 through BMP-13. BMPs are available from Genetics Institute, Inc., Cambridge, Mass. and may also be prepared by one skilled in the art as described in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al. All osteoinductive factors are contemplated whether obtained as above or isolated from bone. Methods for isolating bone morphogenetic protein from bone are described in U.S. Pat. No. 4,294,753 to Urist and Urist et al., 81 PNAS 371, 1984.

The choice of carrier material for the osteogenic composition is based on biocompatibility, biodegradability, mechanical properties and interface properties as well as the structure of the load bearing member. The particular application of the compositions of the invention will define the appropriate formulation. Potential carriers include calcium sulphates, polylactic acids, polyanhydrides, collagen, calcium phosphates, polymeric acrylic esters and demineralized bone. The carrier may be any suitable carrier capable of delivering the proteins. Most preferably, the carrier is capable of being eventually resorbed into the body. One preferred carrier is an absorbable collagen sponge marketed by Integra LifeSciences Corporation under the trade name Helistat® Absorbable Collagen Hemostatic Agent. Another preferred carrier is a biphasic calcium phosphate ceramic. Ceramic blocks are commercially available from Sofamor Danek Group, B. P. 4-62180 Rang-du-Fliers, France and Bioland, 132 Rou d Espangne, 31100 Toulouse, France. The osteoinductive factor is introduced into the carrier in any suitable manner. For example, the carrier may be soaked in a solution containing the factor.

The present invention also provides methods for making the open spacers of this invention. In one embodiment, a method for making an open chambered bone dowel includes obtaining an off-center plug from the diaphysis of a long bone so that the dowel has an open chamber. The open chamber is preferably substantially concave or C-shaped and has an axis that is substantially perpendicular to the long axis of the dowel. Appropriate human source bones include the femur, tibia, fibula, humerus, radius and ulna. Long bones from other species are also contemplated although human source bones are generally preferred for human recipients.

The first step is to identify an acceptable donor based upon appropriate standards for the particular donor and recipient. For example, where the donor is human, some form of consent such as a donor card or written consent from the next of kin is required. Where the recipient is human, the donor must be screened for a wide variety of communicable diseases and pathogens, including human immunodeficiency virus, cytomegalovirus, hepatitis B, hepatitis C and several other pathogens. These tests may be conducted by any of a number of means conventional in the art, including but not limited to ELISA assays, PCR assays, or hemagglutination. Such testing follows the requirements of: (i) American Association of Tissue Banks, Technical Manual for Tissue Banking, Technical Manual—Musculoskeletal Tissues, pages M19-M20; (ii) The Food and Drug Administration, Interim Rule, Federal Register/Vol. 58, No. 238/Tuesday, Dec. 14, 1994/Rules and Regulations/65517, D. Infectious Disease . Testing and Donor Screening; (iii) MMWR/Vol. 43/No. RR-8 m Guidelines for Preventing Transmission of Human Immunodeficiency Virus Through Transplantation of Human Tissue and organs, pages 4-7; (iv) Florida Administrative Weekly, Vol. 10, No. 34, Aug. 21, 1992, 59A-1.001-01459A-1.005(12)(c), F.A.C., (12)(a)-(h), 59A-1.005 (15), F.A.C., (4)(a)-(8). In addition to a battery of standard biomechanical assays, the donor, or their next of kin, is interviewed to ascertain whether the donor engaged in any of a number of high risk behaviors such as having multiple sexual partners, suffering from hemophilia, engaging in intravenous drug use, etc. Once a donor has been ascertained to be acceptable, the bones useful for obtention of the dowels are recovered and cleaned.

Preferably, the bone plugs are obtained using a diamond or hard metal tipped cutting bit which is water cleaned and cooled. Commercially available bits (e.g. core drills) having a generally circular nature and an internal vacant diameter between about 10 mm to about 20 mm are amenable to use for obtention of these bone plugs. Such core drills are available, for example, from Starlite, Inc. In one embodiment, a pneumatic driven miniature lathe having a spring loaded carriage which travels parallel to the cutter is used. The lathe has a drive system which is a pneumatic motor with a valve controller which allows a desired RPM to be set. The carriage rides on two runners which are 1.0 inch stainless rods and has travel distance of approximately 8.0 inches. One runner has set pin holes on the running rod which will stop the carriage from moving when the set pin is placed into the desired hole. The carriage is moveable from side to side with a knob which has graduations for positioning the graft. A vice on the carriage clamps the graft and holds it in place while the dowel is being cut. The vice has a cut-out area in the jaws to allow clearance for the cutter.

In operation, the carriage is manually pulled back and locked in place with a set pin. The graft is loaded into the vice and is aligned with the cutter. Sterile water is used to cool and remove debris from graft and/or dowel as the dowel is being cut. The water travels down through the center of the cutter to irrigate as well as clean the dowel under pressure. After the dowel is cut, sterile water is used to eject the dowel out of the cutter.

Dowels of any size can be prepared according to this, invention. In some embodiments, the dowels range from 5 mm to 30 mm diameters with lengths of about 8 mm to about 36 mm being generally acceptable, although other appropriate gradations in length and diameter are available. For cervical dowels, such as anterior cervical fusion or ACF dowels, lengths of 8 mm, 9 mm, up to about 15 mm are generally desirable. Dowels of differing diameter are most conveniently obtained as follows:

| Diameter | Source |
| --- | --- |
| 10.6-11 mm | fibula |
| 12 mm | radius |
| 14 mm | ulna |
| 14+ mm | small humeri |

Dowels for thoracic and lumbar fusions, such as anterior thoracic inner body fusion (ATIF) and anterior lumbar inner body fusion (ALIF) dowels, respectively, having a depth of between about 10-36 mm, and preferably between about 15-24 mm, are generally acceptable, depending on the needs of a particular patient. Dowels of differing diameter for thoracic and lumbar fusions are most conveniently obtained as follows:

| Diameter | Source |
| --- | --- |
| 14-16 mm | humerus |
| 16–18 mm | femur |
| 18–20 mm | tibia |

While the foregoing diameters and source bones for such dowels is a useful guide, one of the significant advances provided by this invention is that the open-chambered dowel of this invention provides tremendous flexibility with respect to the source bone used.

Since the spacers of the preferred embodiment are obtained from off-center transverse plugs across the diaphysis of long bones, each dowel has the feature of having a substantially "C"-shaped chamber through the dowel perpendicular to the length of the dowel formed by the intersection of the natural intramedullary canal of the source bone and the cutter blade as it forms the plug. The canal cavity in the long bone is, in vivo, filled with bone marrow. In the standard Cloward Dowel and unicortical dowels known in the art, no such natural cavity exists and the cancellous bone that forms the body of such dowels tends to be too brittle to accept machining of such a cavity. The dowels of this invention, by the nature of their origin, inherently define such a cavity. Naturally, based on this disclosure, those skilled in the art will recognize that other bone sources could be used which do not have the intramedullary canal, and if sufficient strength is inherent to the bone, a cavity or chamber could be machined. In addition, it will be appreciated from the instant disclosure that an existing diaphysial cortical dowel (FIG. 3), available from the University of Florida Tissue Bank, Inc., could be modified by machining one side of such a dowel until one wall of the dowel is sufficiently abraded to "break-through", thereby transforming the diaphysial cortical dowel into the "C"-shaped dowel of this invention. Accordingly, such extensions of this invention should be considered as variants of the invention disclosed herein and therefore come within the scope of the claims appended hereto.

The marrow is preferably removed from the intramedullary canal of the diaphysial plugs and the cavity is cleaned, leaving the chamber. The spacer may be provided to the surgeon with the chamber prepacked or empty for the surgeon to pack during surgery. The cavity or chamber can then be packed with an osteogenic material or composition.

The plug is then machined, preferably in a class 10 clean room to the dimensions desired. The machining is preferably conducted on a lathe such as a jeweler's lathe, or machining tools may be specifically designed and adapted for this purpose. Specific tolerances for the dowels and reproducibility of the product dimensions are important features for the successful use of such dowels in the clinical setting.

In some embodiments, the forward end of the dowel which is to be inserted into a cavity formed between adjacent vertebrae is chamfered. The curvature of the chamfered end facilitates insertion of the dowel into the intervertebral space. Chamfering can be accomplished by appropriate means such as by machining, filing, sanding or other abrasive means. The tolerance for the chamfering is fairly liberal and the desired object is merely to round or slightly point the end of the dowel that is to be inserted into the cavity formed between adjacent vertebrae to be fused.

In some embodiments, the invention includes methods for providing surface features into the walls of the dowels. The methods may include defining a tool or instrument attachment hole in an end of the dowel. The hole may be drilled and preferably tapped. Preferably, the dowel will be of such dimensions as to fit standard insertion tools, such as those produced by Sofamor Danek Group, Inc. (1800 Pyramid Place, Memphis, Tenn. 38132, (800) 933-2635). In addition, a score mark or driver slot may be inscribed on the instrument attachment end of the dowel so that the surgeon can align the dowel so that the chamber is parallel with the length of the recipient's spinal column. The mark or slot allows the surgeon to orient the dowel properly after the dowel is inserted and the chamber is no longer visible. In the proper orientation, the endplates of the adjacent vertebrae are exposed to osteogenic material in the chamber. In some embodiments, the driver slot is omitted to preserve as much bone stock, and therefore strength, in the end as possible.

Surface features such as grooves and threads may be preferably defined or inscribed on the outer cylindrical surface of the dowel. Machining of such features on dowels known in the art is difficult if not impossible due to the brittle cancellous nature of such dowels. Accordingly, the dowels of this invention have the advantage of having very good biomechanical properties amenable to such machining.

Figure 18:
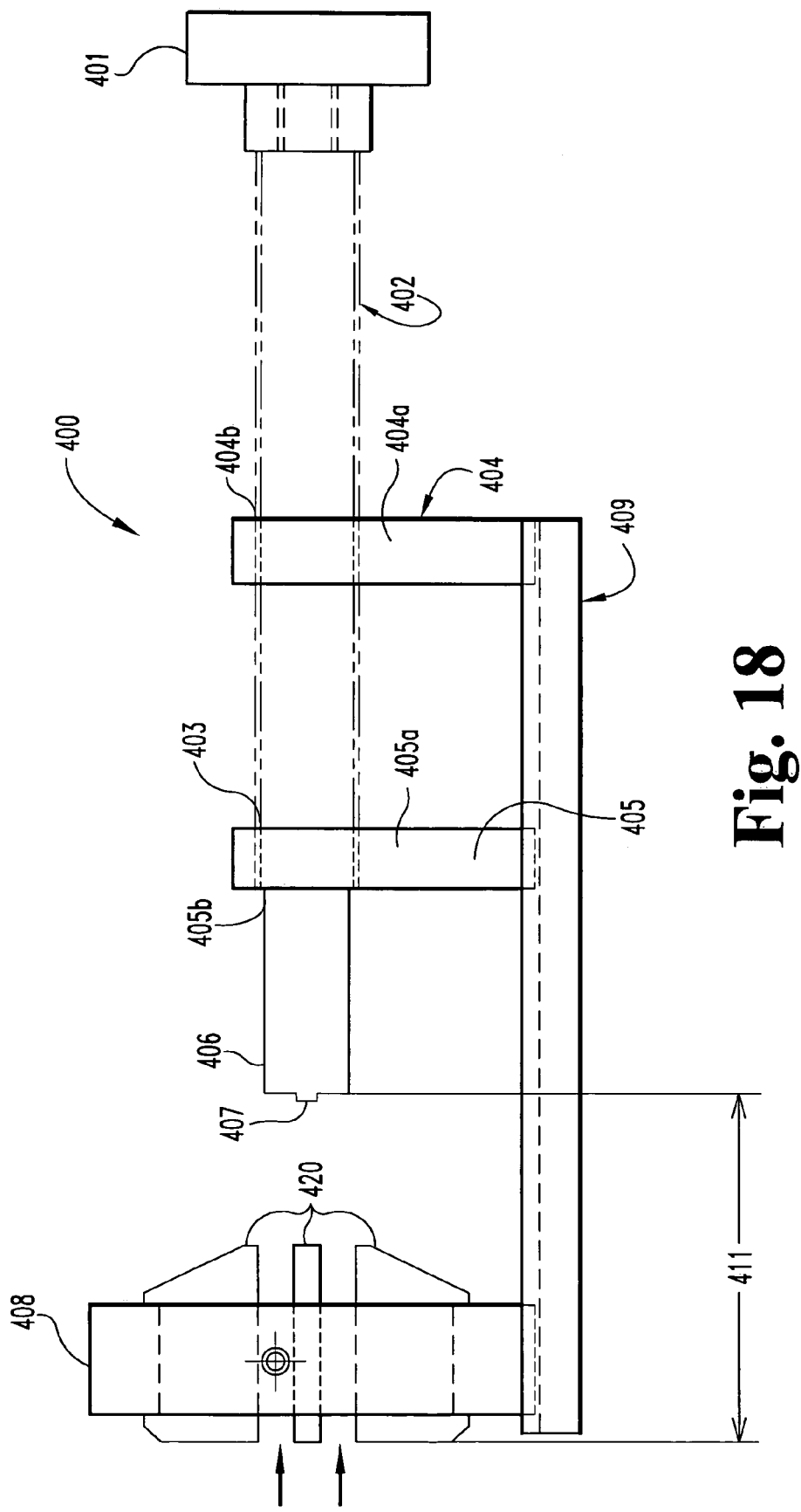
FIG. 18 is a side elevational view of the dowel threader of FIG. 17.
Figure 19:
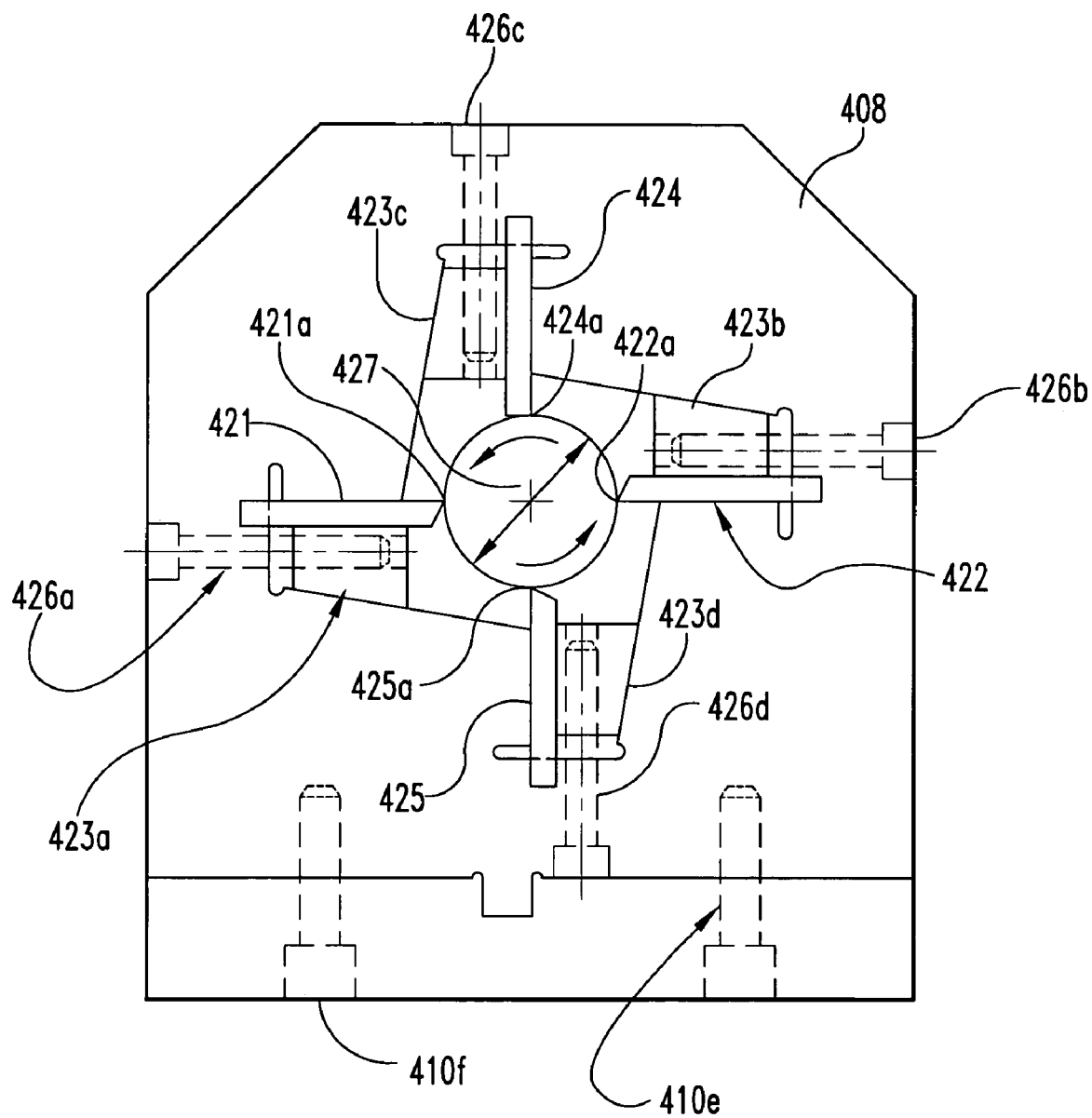
FIG. 19 is an end elevational view of the dowel threader of FIGS. 17 and 18 showing elements of the cutter assembly.

Those skilled in the art will also recognize that any of a number of different means may be employed to produce the threaded or grooved embodiments of the dowel of this invention. However, one preferred embodiment of a thread cutter 400 is depicted in FIGS. 17-23. The cutter 400 includes a drive shaft 402 for supporting a spacer and a cutter assembly 420. The terminal end 406 of the drive shaft 402 includes a spacer engager 407. In one embodiment and as best shown in FIG. 18, the spacer engager 407 is a protruding element which matingly corresponds to the driver slot on the tool end of the open-chambered spacers of this invention. The drive shaft 402 can be turned to rotate and advance the spacer incrementally through the cutter assembly 420 to inscribe a feature such as a thread into the surface of the spacer.

In one embodiment, the drive shaft 402 can be turned by a handle 401 rigidly attached to a first end 402a of the shaft 402. The drive shaft 402 preferably is provided with a graduated segment means for controlled incremental advancement of the drive shaft 402 upon rotation of the handle 401. In this embodiment, the means is a threaded portion 403. Support means 404 and 405 are preferably provided for alignment and support of the shaft 402. Each of the support means 404, 405 include a wall 404a, 405a defining an aperture 404b, 405b. The support means 404, 405 may having controlling means within the apertures 404b, 405b for controlling rotation and incremental advancement of the shaft. In some embodiments, the controlling means include matching threads or bearings.

The thread cutter assembly includes a housing 408 and blades 421, 422 and guide plates 424, 425 mounted within the housing 408. The cutter blades 421, 422 are held in place in the housing 408 by fixation wedges 423a and 423b while guide plates 424 and 425, having no cutting teeth, are held in place by fixation wedges 423c and 423d. Fixation wedges 423a-d are held in place by screws 426a-d. The foregoing arrangement is preferred, as it allows for easy assembly and disassembly of the cutter assembly, removal of the cutter blades, cleaning of the various components, and if desired, sterilization by autoclaving, chemical, irradiative, or like means. The cutter blades 421, 422 and guide plates 424, 425 may be rigidly fixed in place by increasing the tension created by tightening screws 426a-d, which draws the fixation wedges 423a-d into the housing 408, thereby clamping these elements in place. Naturally, based on this disclosure, those skilled in the art will be able to develop equivalents of the cutter assembly system described herein, such as by use of wing-nuts, welding or like means to affix these various elements in appropriate cutting relationship to each other.

Fixation wings 421c and 421d are provided to allow proper seating of the cutter blade upon insertion into the housing 408. At θ a line is provided on cutter blades 421 and 422, which allows for appropriate registration between cutter blades 421 and 422 during manufacture thereof. Upon insertion into the housing 408, it is critical that the blades and the teeth thereon are appropriately registered so that as blade 421 cuts into the bone dowel as it is rotationally advanced through the cutter assembly 420, blade 422 is appropriately situated so that its matching teeth are in phase with the thread inscribed by the teeth on blade 421. This is accomplished by a combination of the fixation wings 421d and 421c properly seating in the housing 408 such that wall 421c abuts the housing 408 and the housing 408 walls abut the insides of wings 421d and 421c.

The cutting edges 421a, 422a of the blades 421, 422 are disposed in relation to each other so that they are on axis. The cutting edges 421a, 422a and the guiding edges 424a, 425a of the guide plates define an aperture 427 for a spacer or dowel. The diameter of the dowel that may be threaded according to this device is defined by the diameter of the aperture 427.

The supports 404 and 405 and the housing 408 for the cutter assembly are all preferably mounted on a steady,. solid, weighty base unit 409 via screws, welding, or like attachment means at 410a-f. The supports and the cutter assembly are configured so that there is an appropriate travel distance 411 from the fully backed out terminal end of the drive shaft 406 to the end of the cutter assembly 420. This distance must be sufficient to allow insertion of a dowel blank and advancement of the blank through the cutter assembly 420 to allow a fully threaded dowel to emerge from the cutter assembly.

Figure 20:
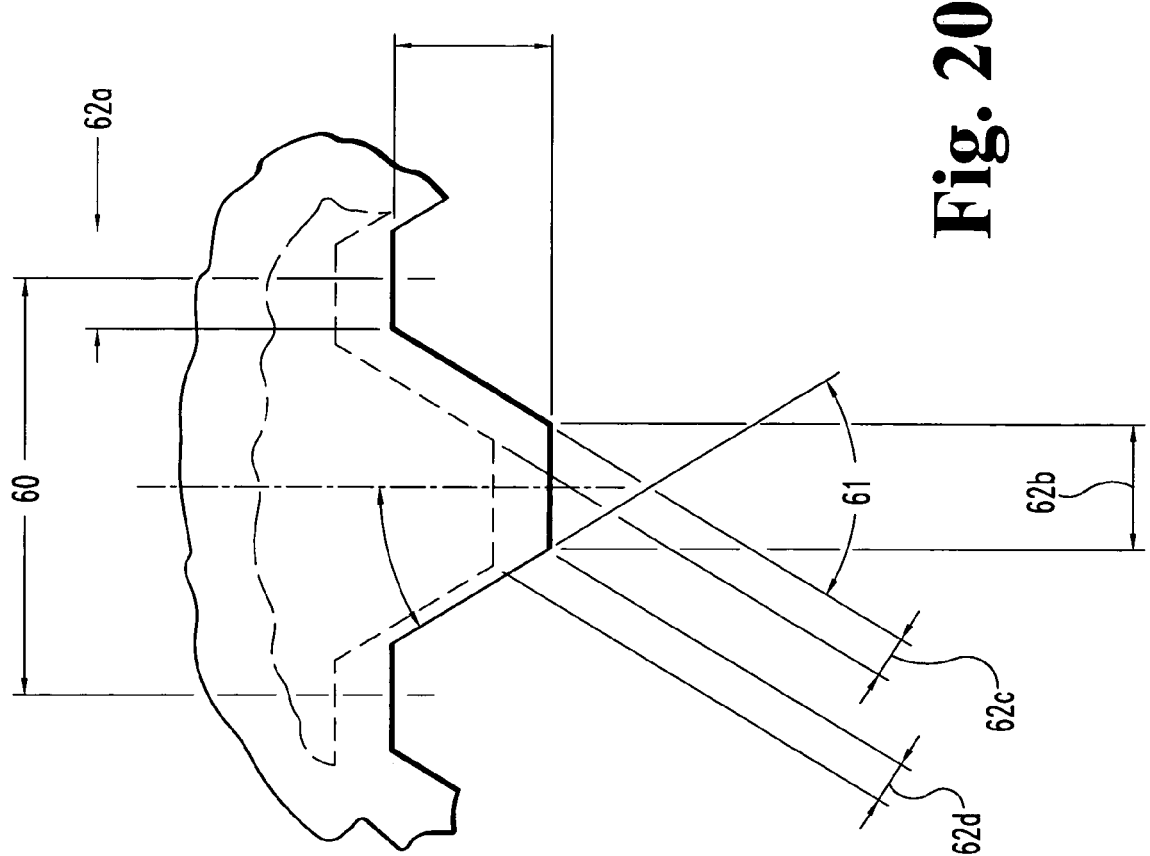
FIG. 20 is a detailed view of a single tooth of one cutter blade of the dowel threader.
Figure 21:
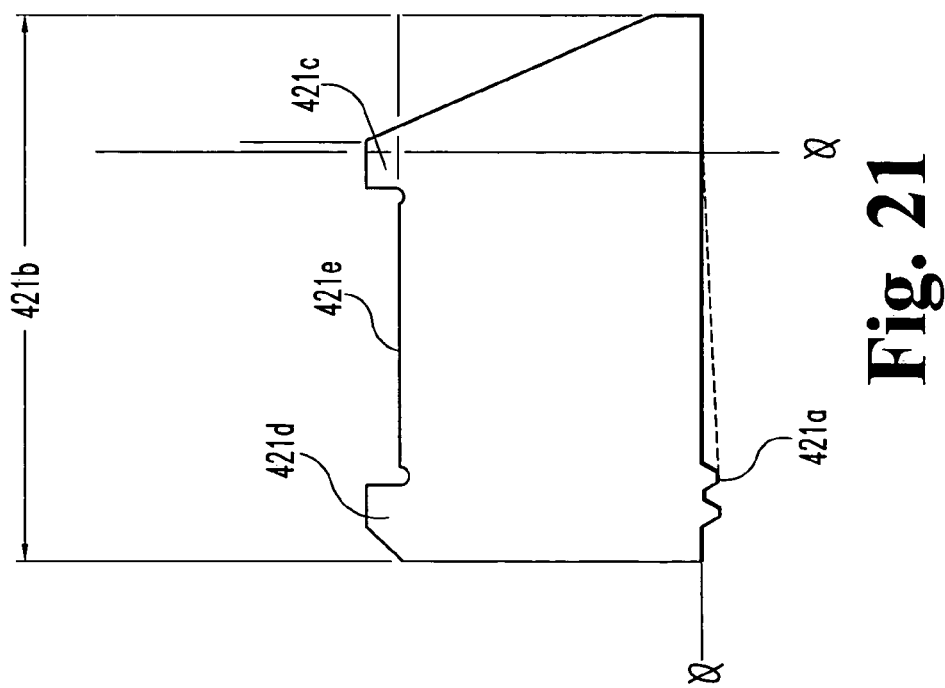
FIG. 21 is a global side view of a cutter blade.

The cutter maintains true tooth form from top to bottom, so that the cutter can be sharpened by surface grinding the face. This is achieved by wire-cutting the teeth such that there is about a 5° incline 62c between the descending vertices at the front and rear of each tooth, and about an 8° incline 62d between the front and rear of the top of each tooth. This aspect can best be seen in FIG. 20. Also, the thickness of the cutter blade, 62c, preferably about 0.100" can be seen in that figure. The angle 61 in FIG. 20 is preferably about 60°. The width of the top of the tooth 62b is preferably about 0.025". The pitch 60 is preferably about 0.100". FIG. 21 shows an overall view of the cutter blades 421 or 422 which are assembled in the cutter assembly housing 408. The entire length of the cutter blade 421b is about 1.650".

Figure 22:
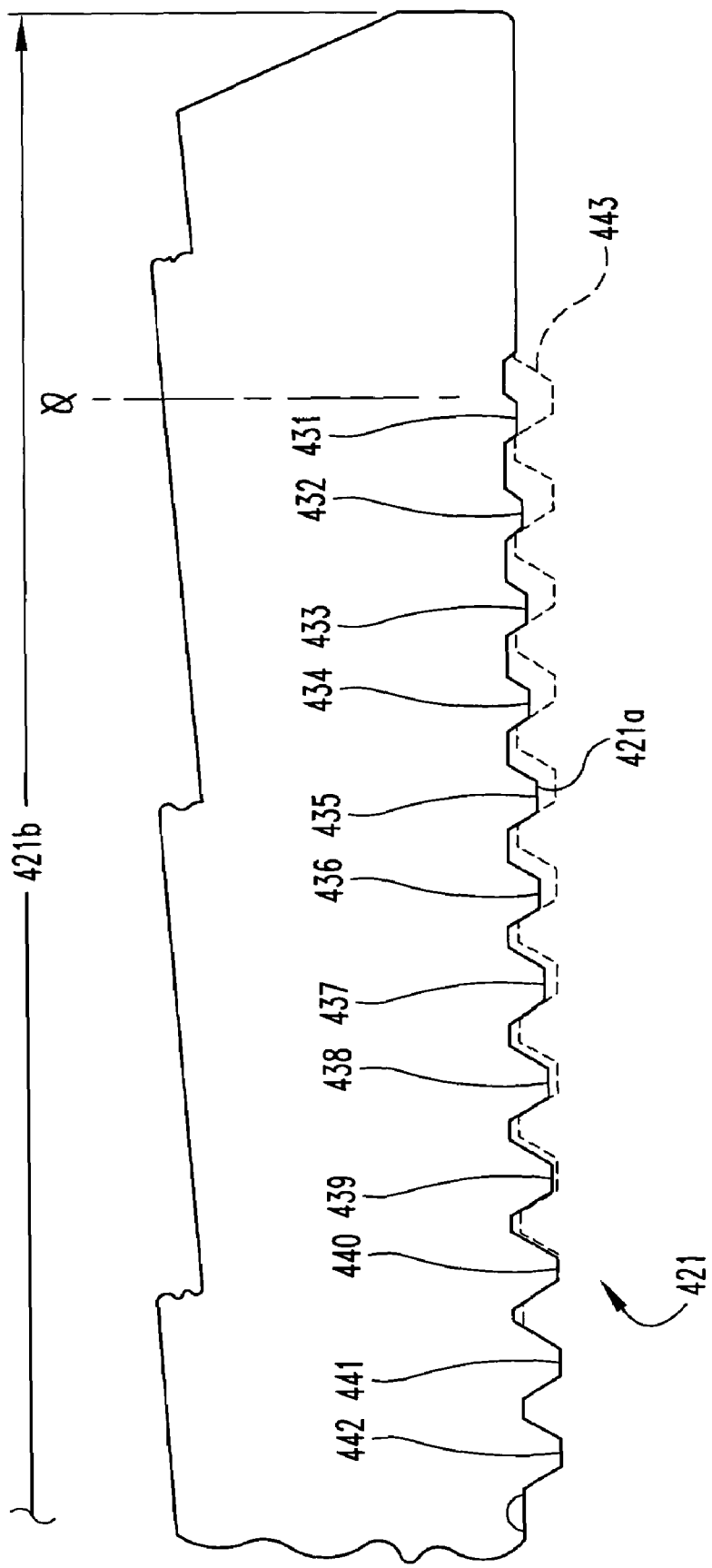
FIG. 22 is a detailed side view of the cutter blade of FIG. 21.
Figure 23:
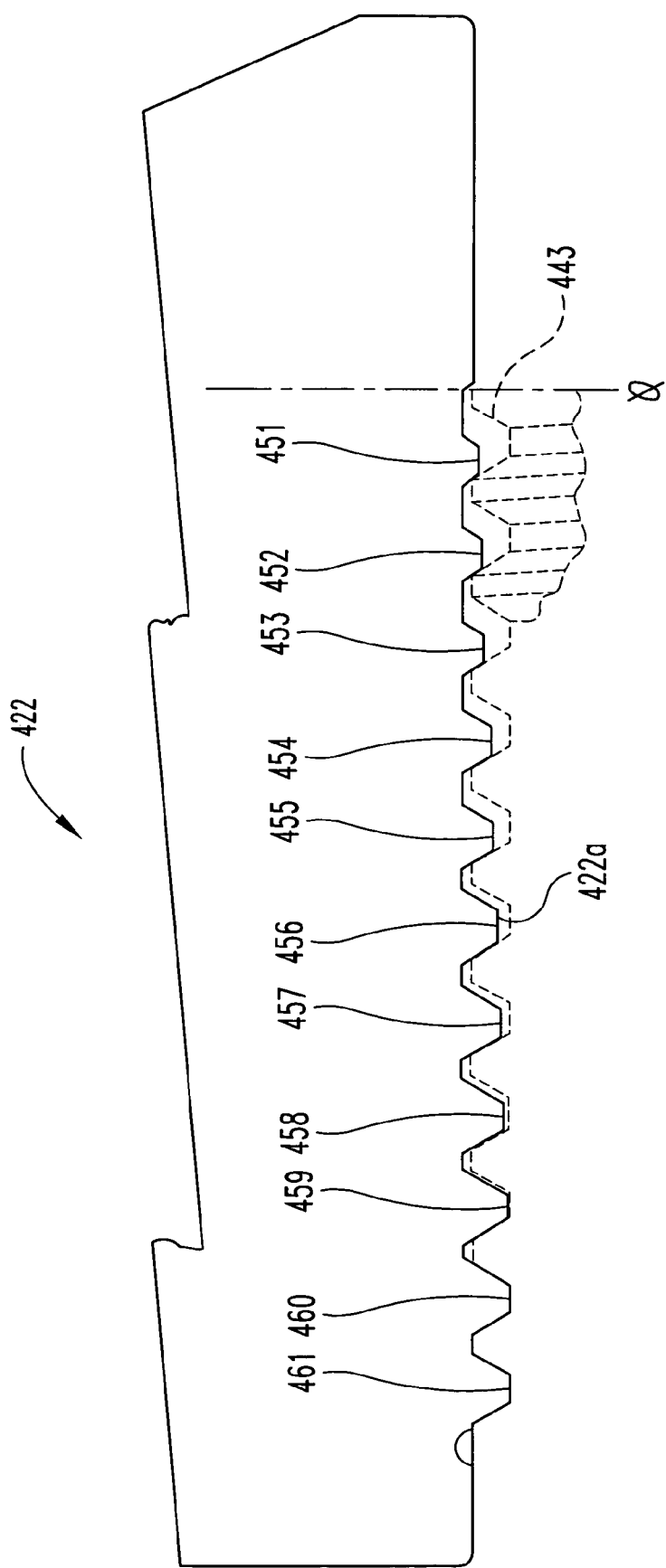
FIG. 23 is a detailed side view of the cutter blade of FIGS. 21 and 22.

Details of the blades 421, 422 are shown in FIGS. 22 and 23. In this embodiment, the cutter blade 421 has twelve cutting teeth 431-442. The cutting edge 422a has eleven teeth 451-461 spread over the length of the blade 422. At 451, the first tooth at 0.004" in this example is encountered by the blank and at each successive tooth, an increase of about 0.004" is made until the final tooth height of about 0.039 is reached at 460 and 461. As a dowel blank is fed into the cutter assembly, it first encounters a truncated tooth at 431, and at every subsequent tooth, the height of the tooth is reached, in this example, of 0.039" at 441 and 442. The truncated teeth 431-440 feed into the dowel being cut along the 300 line so that the teeth cut on only two sides. The dotted line 443 shows the final pitch and form that the cutter will cut in the bone dowel.

It will be recognized by those skilled in the art that all of the foregoing elements should preferably be manufactured from durable materials such as 440 stainless steel, or like materials. In particular, the cutting surfaces 421a and 422a of the blades 421 and 422 are made from hard metal.

In operation, based on the foregoing description, it will be appreciated that the cutter blades 421 and 422 are placed into the housing 408, clamped into place via the fixation wedges 423a, b and the screws 426a, b after the blades have been properly seated and the two blades are perfectly aligned. A blank dowel is then loaded into the orifice 427 and the drive shaft with the protruding element 408 is inserted into a drive slot a dowel. As the handle 401 is turned, the drive shaft forces the dowel to rotate and advance incrementally through the cutter assembly 420, thereby inscribing the thread defined by the cutter blades 421 and 422 into the outer cylindrical surface or circumference of the dowel.

As noted above, those skilled in the art will recognize that modifications to the specifics of the device described will allow for the preparation of the varied threads or grooves in the circumference of the dowel. For example, to form a groove in a dowel, the dowel could be mounted in a lathe, such as those known in the art and commercially available, for example from SHERLINE PRODUCTS, INC., SAN MARCOS, Calif. 92069, and a cutter blade applied as the dowel is rotated.

The final machined product may be stored, frozen or freeze-dried and vacuum sealed as known in the art for later use.

The spacers of this invention may be conveniently implanted with known instruments and tools. Any instrument which will firmly hold the implant and permit the implant to be inserted is contemplated. Preferably, the instrument will be adapted to compensate for the open structure of the spacers of this invention.

Figure 26:
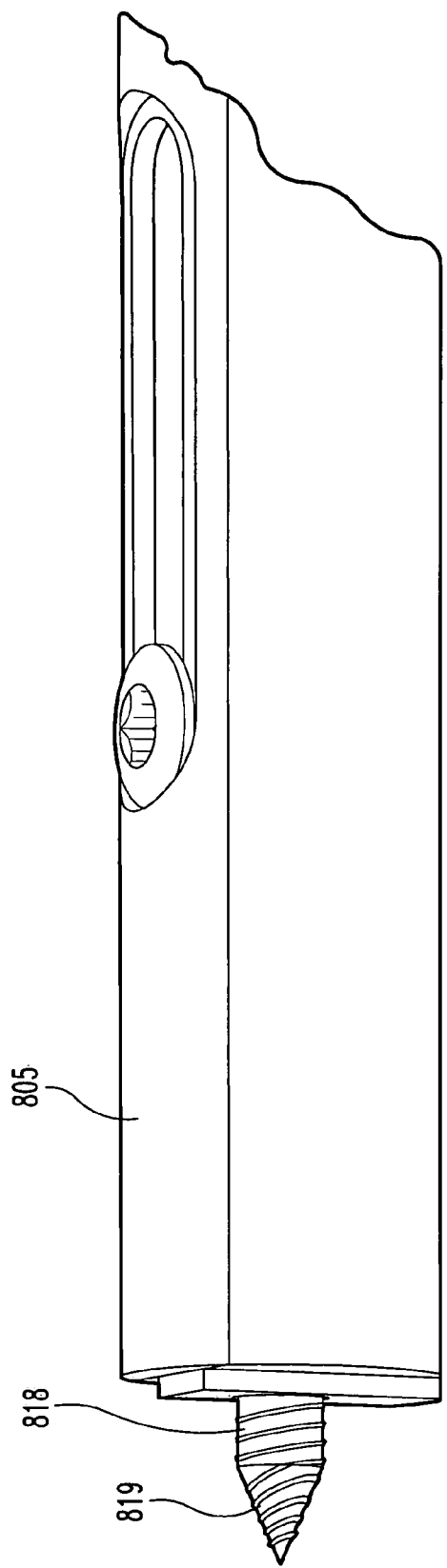
FIG. 26 is a perspective view of a spacer engaging element of an insertion tool.

The present invention further contemplates insertion devices for facilitating the implantation of spacers, implants or bone graft. The tools include spacer engaging means for engaging a spacer or other item and occlusion means for blocking an opening defined in the spacer. One embodiment of an insertion tool of this invention is depicted in FIGS. 24-26.

In one embodiment, an insertion tool 800 is provided which includes a housing 805 having a proximal end 806 and an opposite distal end 807 and defining a passageway 810 between the two ends. A shaft 815 which has a first end 816 and an opposite second end 817 is disposed within the passageway 810. The first end 816 of the shaft 815 is adjacent the distal end 807 of the housing 805. The first end 816 defines a spacer engager 819. An occlusion member 820 is attached to the housing 805.

Figure 27:
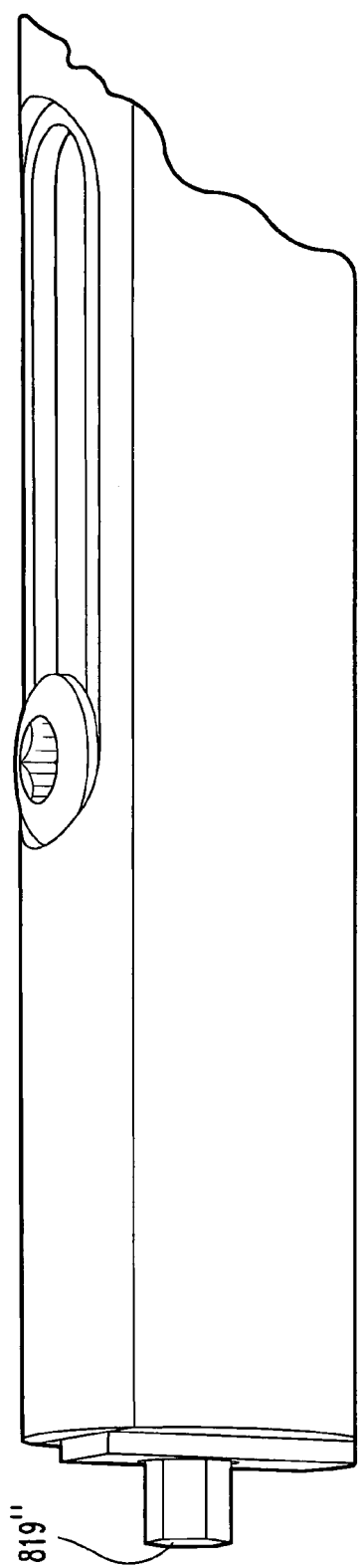
FIG. 27 is a perspective view of a spacer engaging element of an insertion tool.

The spacer engager 819 has any configuration which will engage a spacer. In some embodiments the spacer engager 819 includes a post 818 as shown in FIG. 26 for engaging a hole in the spacer. The post 818 may have any configuration which will provide for mating engagement with a hole in a spacer. For example, in preferred embodiments, the engager 819 is threaded as shown in FIG. 26 to matingly engage a threaded tool hole. Other embodiments include sharply pointed tip 819 as shown in FIG. 24 or a hexagonal shaped tip 819" (FIG. 27). In each case, the engager is shaped and sized to mate engagingly with the tool hole of the spacer. In other embodiments, the spacer engaging means is a pair of prongs having opposite facing spacer engaging members for grasping an outer surface of the spacer.

Figure 28:
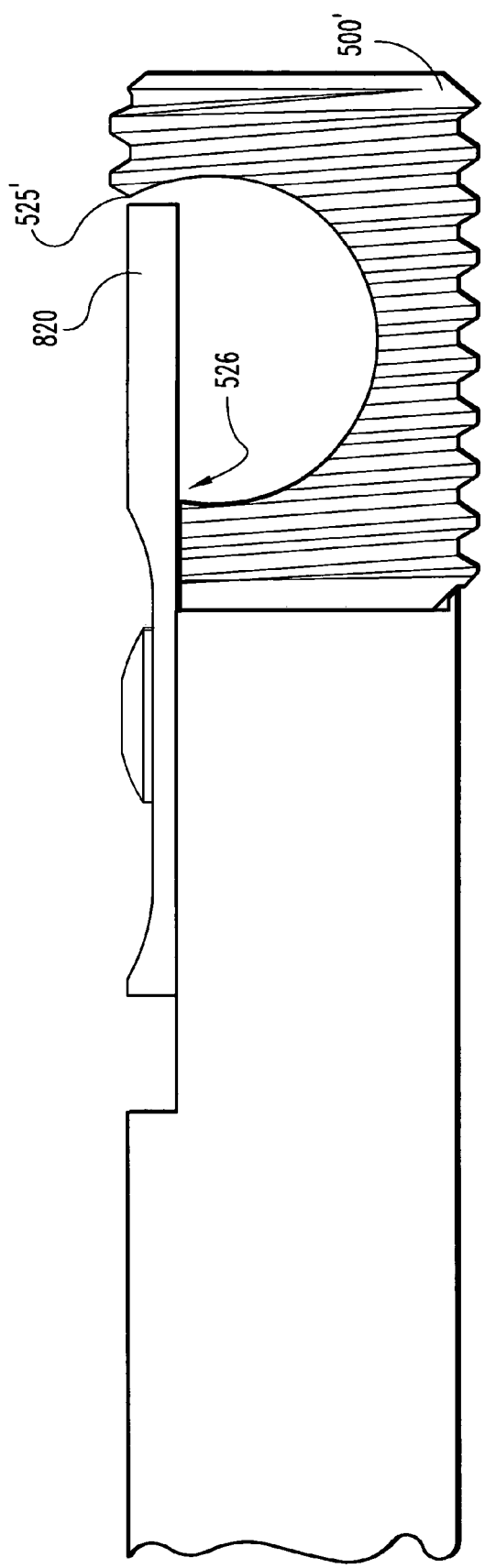
FIG. 28 is a side elevational view of an insertion tool engaged to a spacer.

The spacer insertion tool 800 also includes an occlusion member 820 for blocking an opening defined in the spacer when the spacer engager 819 is engaged to the spacer. In a preferred embodiment, the occlusion member 820 is extendable from the distal end 807 of the housing 805 for blocking an opening in the spacer. As shown in FIG. 28, the occlusion member 820 closes the mouth 525, and channel 526 defined in the spacer 500'.

Figure 29:
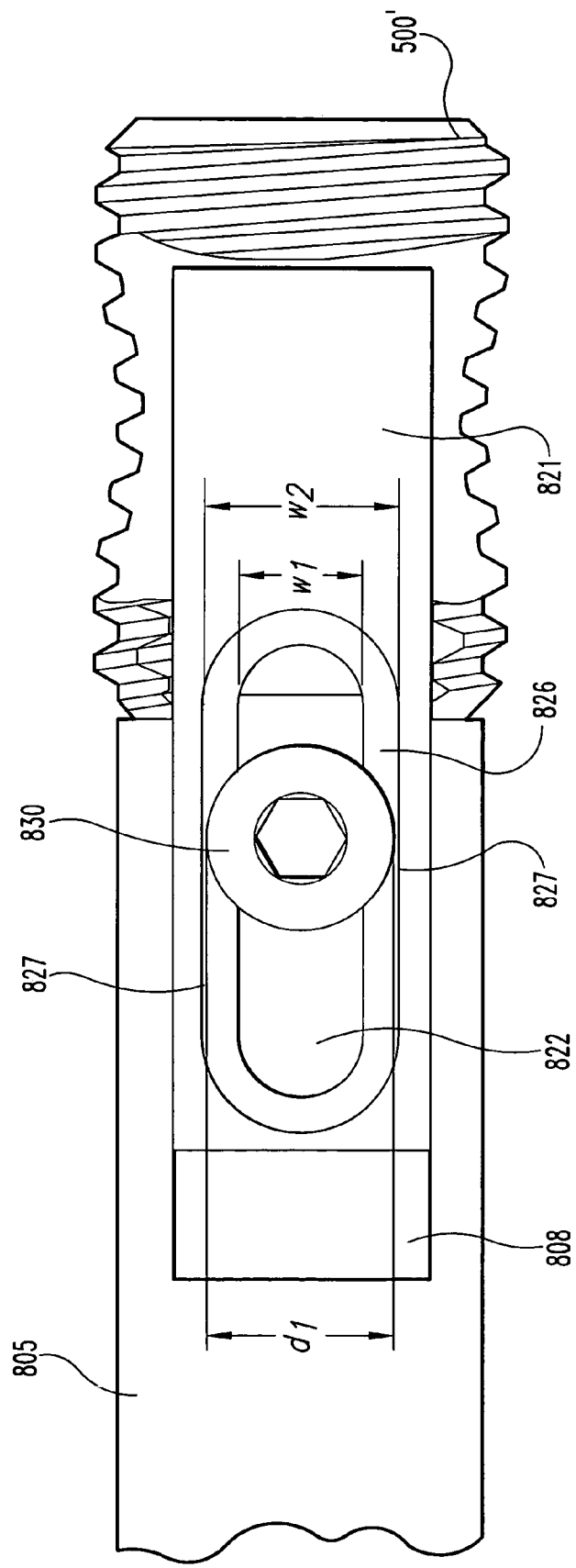
FIG. 29 is a top perspective view of the view shown in FIG. 28.

The occlusion member 820 is preferably slideably engaged to the housing 805. Referring now to FIG. 29, in one embodiment, the occlusion member 820 includes a plate 821 which defines a groove 822. A fastener 830 is engaged to a fastener bore 809 in the housing 805 and the groove 822 is disposed around the fastener 830. In this way, the plate 821 is slideable relative to the housing 805.

Figure 30:
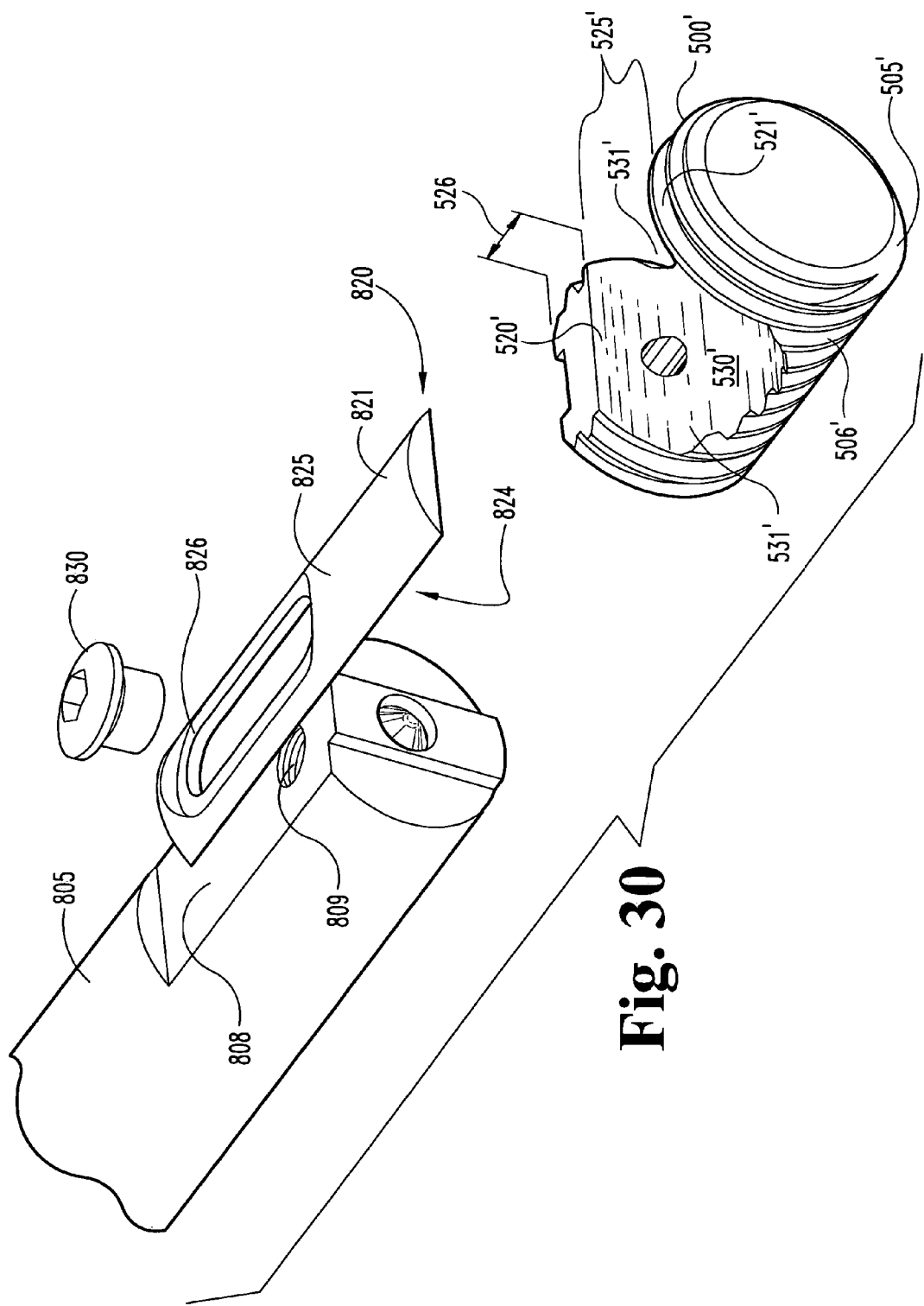
FIG. 30 is an exploded side perspective view of a tool-spacer assembly according to this invention.
Figure 31:
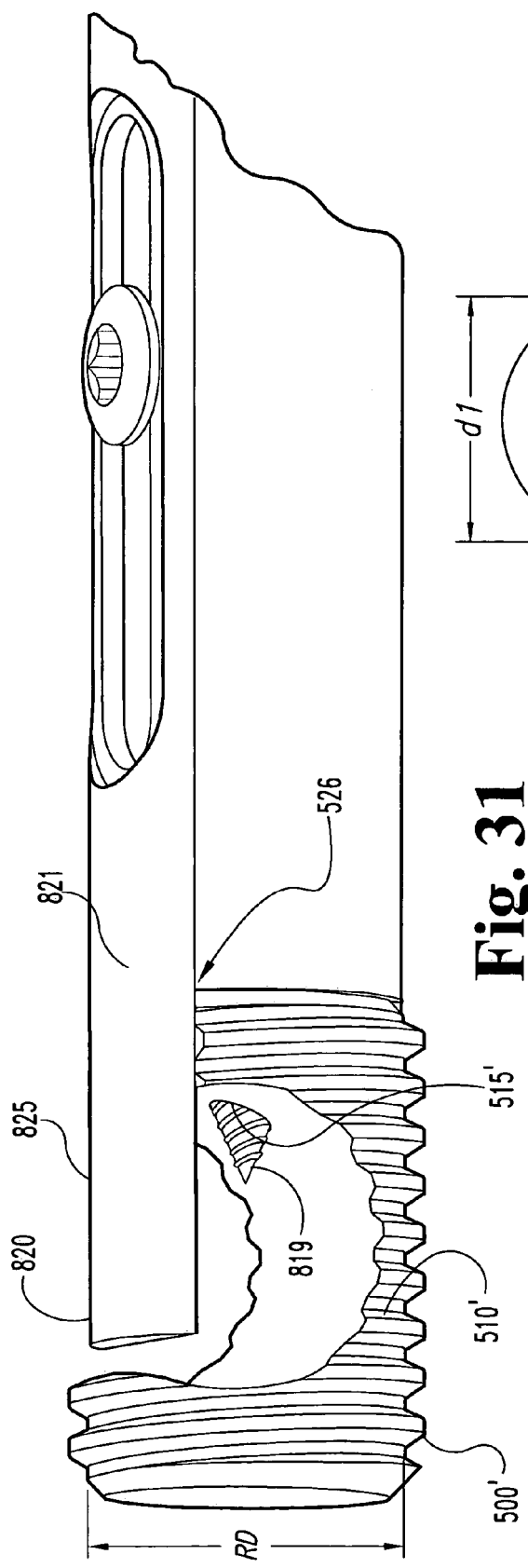
FIG. 31 is a side perspective view of a tool-spacer assembly.

As shown in FIG. 30, the housing 805 is preferably provided with a recess 808 which is defined to accept the occlusion member 820 without increasing the effective diameter of the device 800. The occlusion member is also adapted for the best fit with the spacer. For example, the interior surface 824 of the occlusion member would be curved to complement the scalloped faces 582 and 583 shown in FIG. 11 for crescent engagement. Referring now to FIGS. 30 and 31, the plate 821 of the occlusion member 820 preferably includes a curved superior surface 825 which approximates and completes the minor diameter of the dowel 500' when the spacer engager 819 is engaged to the tool engaging hole 515' and the occlusion member 820 is blocking the channel 526 of the spacer 500'. Preferably, the plate 821 and the arm 520' of the spacer 500' will be configured such that the plate 821 will not extend beyond the channel 526 when the tool 800 is engaged to the spacer 500'. In other words, the curved superior surface 825 will not increase the effective root diameter RD of the threaded outer surface 510'. This facilitates rotation and screw insertion of the spacer and occlusion member combination into an intervertebral space.

The tool 800 depicted in FIG. 24 also includes a handle portion 840. The handle portion includes means for slidingly moving the shaft 815 within the housing 805 and for rotating the post 818. In the embodiment shown in FIGS. 24 and 25 the means includes a thumbwheel 841. In some embodiments, the handle portion 840 has a Hudson end attachment 842.

Figure 32:
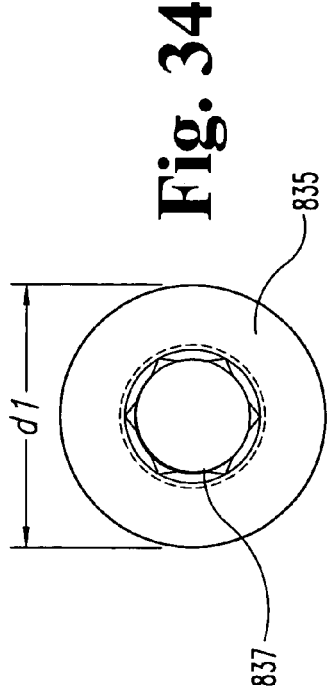
FIG. 32 is a top perspective view of a fastener of this invention.
Figure 33:
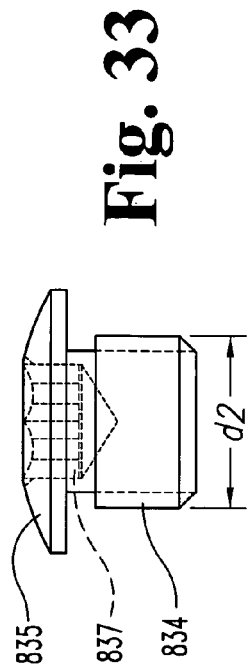
FIG. 33 is a side elevational view of the fastener of FIG. 32.
Figure 34:
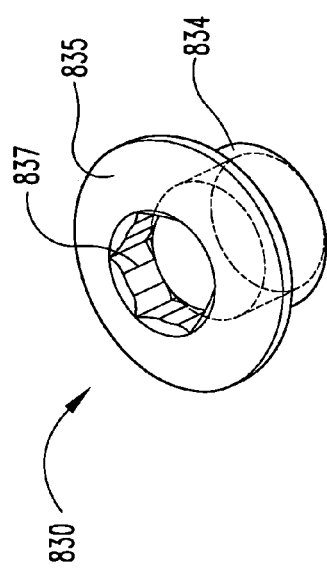
FIG. 34 is a top elevational view of the fastener of FIGS. 32 and 33.

Referring now to FIGS. 32-34, the fastener 830 is preferably provided with a housing engaging means shown in FIG. 32 as a post 834, and a plate engaging means or head portion 835. The fastener 830 preferably includes an internal hex 837 for receiving a fastener driving tool. The post portion 834 may be threaded for mating engagement with threaded bore 809 in the housing 805. In preferred embodiments shown in FIGS. 29 and 30, the plate 821 defines a recess 826 surrounding the groove 822. The diameter d1 of the head portion 835 is greater than the diameter d2 of the post 834. The diameter d2 is less than the width w1 of the groove 822. The diameter d1 of the head portion is greater than width w1 but preferably no greater than the distance w2 between the outer edges 827 of the recess 826. Thus, the head portion 835 of the fastener 830 can rest on the recess 826 while the post portion 834 extends through the groove 822. In this way, plate 821 is slidable relative to the housing 805. This also provides for a low profile device which can be inserted into various cannula for percutaneous procedures.

The spacers and tools in this invention can be conveniently incorporated into known surgical, preferably minimally invasive, procedures. The spacers of this invention can be inserted using laparoscopic technology as described in Sofamor Danek USA's *Laparoscopic Bone Dowel Surgical Technique*,© 1995, 1800 Pyramid Place, Memphis, Tenn. 38132, 1-800-933-2635, preferably in combination with the insertion tool 800 of this invention. Spacers of this invention can be conveniently incorporated into Sofamor Danek's laparoscopic bone dowel system that facilitates anterior interbody fusions with an approach that is much less surgically morbid than the standard open anterior retroperitoneal approaches. This system includes templates, trephines, dilators, reamers, ports and other devices required for laparoscopic dowel insertion. Alternatively, a minimally invasive open anterior approach using Sofamor Danek's open anterior bone dowel instrumentation or a posterior surgical approach using Sofamor Danke's posterior approach bone dowel instrumentation are contemplated.

The present invention also includes methods for fusing adjacent vertebrae. The spine may be approached from any direction indicated by the circumstances. The vertebrae and the intervertebral space are prepared according to conventional procedures to receive the spacer. A spacer of the appropriate dimensions is selected by the surgeon, based on the size of the cavity created and the needs of the particular patient undergoing the fusion. The spacer is mounted on an instrument, preferably via an instrument attachment hole. In one embodiment, an osteogenic material is placed within the chamber of the spacer and the channel and or mouth of the spacer is then blocked with an occlusion member of the instrument. The spacer is then inserted into the cavity created between the adjacent vertebra to be fused. The spacer is oriented within the intervertebral space so the osteogenic material in the chamber is in communication with the end plates of the vertebra. Once the spacer is properly oriented within the intervertebral space, the occlusion member of the instrument can be withdrawn from the spacer aperture and the spacer engager is disengaged from the spacer.

In some embodiments, osteogenic material is packed into the chamber through the channel after implantation. In still other embodiments, a second spacer is implanted into the intervertebral space. FIG. 8 depicts placement of two dowels of this invention implanted from an anterior approach, while FIG. 9 shows bilateral placement of dowels from a posterior approach. In each case the channel 526 opens adjacent the tool engaging end 501' allowing access to the chamber 530' from either the anterior or posterior approach.

The combination of spacers of this invention with the tools of this invention allow the spacers to provide the benefits of an open spacer without suffering any biomechanical disadvantage or increased fiddle factor. The occlusion member 825 blocks the mouth or channel to lessen the stress on the wall of the spacer for smooth insertion. The occlusion member also allows the chamber to be packed with osteogenic material before the spacers are implanted. Once the spacer is implanted and the occlusion member is withdrawn, additional osteogenic material can be packed into the chamber or around the spacers. In some procedures two open spacers are packed with the mouths facing one another as depicted in FIG. 8. The open mouth of the spacers along with the tools of this invention allow the spacers to be packed closely together because virtually no clearance is required for the insertion tool. The open mouth also allows the chambers to be packed after the spacer is implanted. This is greatly enhanced when one of the arms is truncated, leaving a channel from outside the disc space to the chamber as shown in FIG. 10.

It has been found that certain dimensions are preferred when a spacer of this invention is a bone dowel. For the substantially "C"-shaped chamber, 530, a regular or irregular hole having a diameter no greater than about 0.551" (14 mm) is preferred with a minimum wall thickness 570 at the root of the thread of preferably no less than about 5 mm. Those skilled in the art will recognize that the foregoing specifics, while preferable, may be modified depending on the particular surgical requirement of a given application.

In another specific embodiment, depicted in FIGS. 35-38, the diameter D1 of the dowel is 18 mm and the length L1 is 36 mm. In this specific embodiment, the length L2 of the solid side is shorter than the length of the open side L1 due to the natural curve of the bone. The shorter length L2 is preferably at least 30% of the longer length L1. The length of the truncated arm is preferably between about 50-85% of the diameter of the dowel D1. In this embodiment, the insertion end of the dowel includes a flattened-portion F1. The length of the flattened portion F1 is preferably at least 70% of the diameter of the dowel D1. As best shown in FIG. 36, the depth E1a, E1b, E2a, E2b of the end-caps or insertion end and tool engaging ends of the dowel are preferably at least about 3 mm. The depth of the bevel B2 of the threads is preferably 1 mm while the bevel angle B1 is preferably about 45 degrees. The depth of the drive slot C2 is preferably about 1.5 mm deep and the width C1 is about 5.5 mm. The diameter D2 of the tapped instrument attachment hole is about 3.3 mm with T5 indicating the tapped thread.

Figure 39:
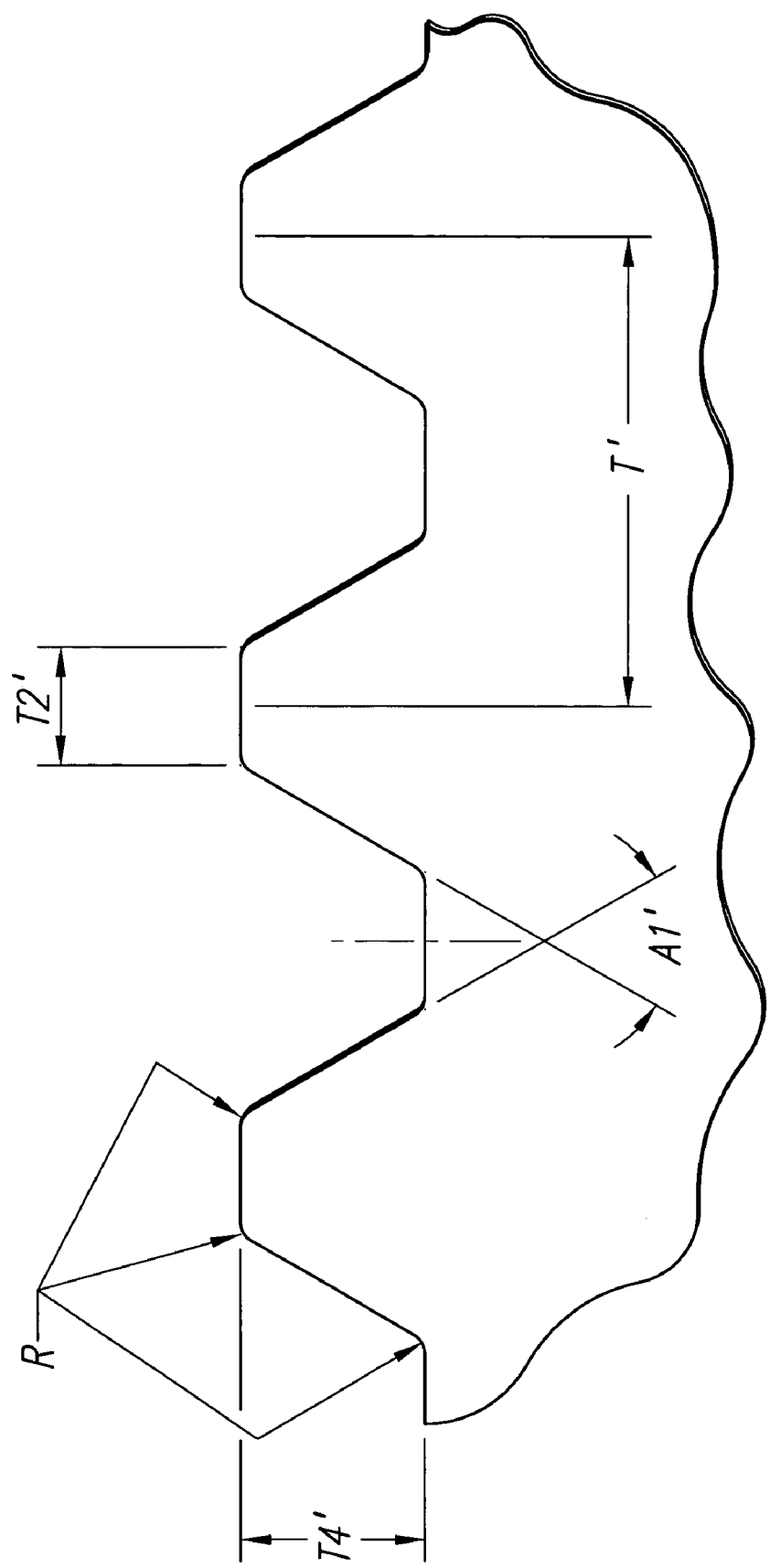
FIG. 39 is a detail of one embodiment of the thread of one embodiment of the threaded dowel of this invention.

Various surface feature configurations are contemplated by this invention. Referring now to FIG. 38, a detail of the thread of one embodiment is provided. The thread pitch T1 is about 2.5 mm. The length T2 of the top of each tooth of the thread is about 0.6 mm, the depth T4 of the thread is about 1 mm and the width T3 of the thread at the thread root is about 0.8 mm. The outer thread angle A3 is about 60 degrees in this embodiment. FIG. 39 shows a detail of a portion of a threaded dowel of another embodiment which has ten right handed threads per inch at a helix angle at the root diameter of about 2.8892°. In this specific embodiment, the pitch T1' is 0.100"; the thread angle A1' is 60°; the thread crest width T2' is 0.025"; the thread height T4' is 0.039"; and the radius of the various thread angle as it changes R is typically about 0.010".

While the foregoing description discloses specific aspects of this invention, those skilled in the art will recognize that any of a number of variations on the basic theme disclosed herein can be made. It is contemplated that the spacers of this invention can be formed of any suitable biocompatible material, including metals, ceramics, polymers, composites, alloys and the like. Some embodiments include titanium, stainless steel, and Hedrocel®. Thus, for example, differing shapes can be made from the diaphysis of various bones and could be used for other orthopaedic purposes than vertebral fusions. In addition, any of a number of known bone treatments can be applied to the dowel of this invention to alter its properties. For example, the methods disclosed in U.S. Pat. Nos. 4,627,853; 5,053,049; 5,306,303 and 5,171,279 can be adapted and applied to the invention disclosed herein. Accordingly the disclosures of those patents is herein incorporated by reference for this purpose.

Having described the dowel of this invention, its mode of manufacture and use, the following specific examples are provided by way of further exemplification and should not be interpreted as limiting on the scope of the invention herein disclosed and claimed.

EXAMPLES

Example-1

Torsional Testing of "C"-Shaped Dowel

The C-shaped dowel of this invention was tested and the following measurements made of the dowel's ability to withstand insertional torque. The data presented here are for the 16 mm dowel. However, similar results are expected for other lengths of the dowel of this invention. For each dowel, a measured torque is applied to the dowel as it is maintained in a stationary position. For biological insertion of dowels, torques no higher than about 1 newton-meter are expected. The various dimensions measured in the following table correspond to the dimension shown in FIGS. 35-38:

| Sample | Diam. (mm) D1 | OD (mm) W1 | ID (mm) W1* | Height (mm) H** | Calc. Thickness*** | % diff. Meas.-Calc. | Failure Torque | Failure Type |
|---|---|---|---|---|---|---|---|---|
| 1 | 15.8 | 5.1 | 4.6 | 13.2 | 4.0 | 15 | 4.00 | s. wall |
| 2 | 15.8 | 5.5 | 4.8 | 13.2 | 4.0 | 19 | 3.5 | s. wall |
| 3 | 15.9 | 6.2 | 5.3 | 13.4 | 4.3 | 25 | 3.89 | slot |
| 4 | 15.9 | 7 | 6.3 | 14.1 | 5.1 | 23 | 4.95 | slot |
| 5 | 15.6 | 5.8 | 5.4 | 13.6 | 4.5 | 21 | 5.2 | s. wall |
| 6 | 15.8 | 5.5 | 4.9 | 13.1 | 4.0 | 24 | 4.36 | s. wall |
| 7 | 15.7 | 5.8 | 5.4 | 13.4 | 4.3 | 27 | 4.00 | slot |

W1* = W1-T4;
H** = see H1-H4, FIG. 16;
calc. thickness*** = theoretical calculations based on sidewall height, H From these data, it is clear that dowels of this invention are able to withstand considerably more than the 1 newton-meter of torque required to insert the dowel in physiological situations. From theoretical calculations based on the sidewall height, the difference between the calculated sidewall thickness and the measured thickness was found to be, on average, about 22%, leading to the conclusion that only approximately 22% the measured thickness is cancellous bone, and the substantial majority of the bone is cortical bone.

Example 2

Compression Testing

The "C"-shaped dowel of this invention was compressively tested and the load to failure was measured. It is anticipated that loads no higher than about 10,000 newtons are likely to be experienced in-place in the vertebral column. Compression testing of several different "C"-shaped dowels of this invention indicated that dowels of this invention survive axial compression loads significantly higher than the 15,000 newton threshold:

| # | Thread | Avg D1 | L1 | E2a | E2b | Avg E2 | E1a | E1b | Avg E1 | mass g | Failure Load (N) |
|---|---|---|---|---|---|---|---|---|---|---|---|
| 1 | no | 15.9 | 25.5 | 5.3 | 4.7 | 5.0 | 3.9 | 4.4 | 4.2 | 4.193 | 4372 |
| 2 | yes | 15.9 | 23.7 | 5.1 | 5.1 | 5.1 | 4.2 | 5.0 | 4.6 | 4.073 | 13502 |
| 3 | no | 15.9 | 23.7 | 4.8 | 5.3 | 5.1 | 3.8 | 2.6 | 3.3 | 4.035 | 13748 |
| 4 | yes | 15.9 | 22.5 | 7.1 | 7.0 | 7.1 | 7.0 | 5.4 | 6.2 | 5.075 | 20940 |
| 5 | poor | 16.0 | 23.4 | 5.6 | 5.4 | 5.5 | 5.8 | 6.2 | 6.0 | 4.986 | 22420 |
| 6 | yes | 15.7 | 26.1 | 7.1 | 7.1 | 7.1 | 8.4 | 8.6 | 8.5 | 5.331 | 24500 |
| 7 | yes | 16.8 | 23.8 | 5.4 | 5.0 | 5.2 | 6.0 | 6.0 | 6.0 | 3.928 | 14389 |
| 8 | yes | 17.6 | 22.4 | 4.8 | 5.5 | 5.2 | 5.8 | 4.6 | 5.2 | 5.448 | 16730 |
| 9 | poor | 16.9 | 22.2 | 6.7 | 5.2 | 8.0 | 6.4 | 4.7 | 5.1 | 5.226 | 19576 |
| 10 | poor | 17.9 | 28.3 | 7.8 | 7.2 | 7.5 | 7.6 | 7.2 | 7.4 | 6.201 | 20606 |
| 11 | yes | 17.9 | 21.2 | 4.9 | 6.8 | 5.9 | 4.5 | 4.4 | 4.5 | 5.654 | 21461 |
| 12 | yes | 17.8 | 23.6 | 6.6 | 6.3 | 6.5 | 6.0 | 5.4 | 5.7 | 5.706 | 23971 |
| 13 | yes | 19.9 | 25.6 | 6.3 | 6.6 | 6.5 | 6.4 | 6.4 | 6.4 | 7.915 | 24761 |

The mean load to failure of these dowels is 18544 newtons, indicating that on average, more dowels can withstand 15000 newtons axial pressure than not. These data also indicate the need for diligent quality control to eliminate dowels that do not withstand minimal axial compression loads from being implanted.

Example 3

Cervical Fusion Using "C"-Shaped Dowel

Preoperative Diagnosis. Ruptured cervical disc and spondylosis C5-6.

Operative Procedure. Anterior cervical discectomy and fusion C5-6.

After satisfactory general endotracheal anesthesia in the supine position, the patient is prepped and draped in the routine fusion. Incision is made in the skin length of the neck and carried through the platysma muscle. Dissection is carried down to expose the anterior vertebral column and the appropriate space identified by x-ray. Discectomy and foraminotomy are then performed and there is found a central, extruded fragment of disc toward the right side. When adequate decompression is achieved, a "C"-shaped dowel is cut from bone bank fibular and counter-sunk between the vertebral bodies to afford distraction. The wound is then irrigated with Bacitracin and closed in layers with Dexon and sterile strips.

Postoperative evaluation and subsequent patient monitoring reveals successful operative outcome and good vertebral fusion.

It should be understood that the example and embodiments described herein are for illustrative purposes only and that various modifications or changes in light thereof will be suggested to persons skilled in the art and are to be included within the spirit and purview of this application and the scope of the appended claims.

What is claimed is:

1. A method for fusing two adjacent vertebrae, comprising the steps of:
   providing a spacer formed of cortical bone, the spacer including a body having a wall, said wall having an outer surface including a concave portion defining a chamber, an opening in communication with said chamber, and a channel defined in said wall in communication with said chamber and said outer surface;
   preparing the vertebrae and the intervertebral space between the vertebrae to receive the spacer; and
   placing the spacer into the intervertebral space.

2. The method of claim 1 wherein said outer surface includes a curved portion and a flattened portion.

3. The method of claim 1 wherein said body further comprises an outer surface that defines a curved portion and a flattened portion.

4. A method for fusing two adjacent vertebrae, said method comprising:
   preparing a space between the two adjacent vertebrae to receive a graft;
   providing a graft composed of cortical bone and comprising an elongated body having an outer surface and a longitudinal axis along a length of said body, said outer surface including a chamber having a substantially concave surface and extending along a second axis substantially perpendicular to said longitudinal axis, said graft defining a channel extending between said chamber and said outer surface in a direction transverse to said second axis; and
   implanting the graft in the space between the two adjacent vertebrae.

5. The method of claim 4 wherein said preparing comprises performing a discectomy on a patient in need thereof.

6. The method of claim 4 wherein the outer surface of the body defines threaded bone engaging portions.

7. A method for fusing two adjacent vertebrae, said method comprising:
   preparing a space between the two adjacent vertebrae to receive a graft;
   providing a graft composed of cortical bone and comprising an elongated body having an outer surface and a longitudinal axis alone a length of said body, said outer surface including a chamber having a substantially concave surface and extending along a second axis substantially perpendicular to said longitudinal axis, wherein the body includes a C-shaped wall defining the chamber; and
   implanting the graft in the space between the two adjacent vertebrae.

8. The method of claim 4 wherein said graft is a bone dowel obtained from the diaphysis of a long bone having a medullary canal, said chamber including a portion of the canal.

9. The method of claim 4 wherein said body comprises upper and lower flattened portions.

10. The method of claim 4 wherein the outer surface comprises vertebrae engaging surfaces.

11. The method of claim 4 wherein the vertebrae engaging surfaces comprise ribs, grooves or threads.

12. The method of claim 4 further comprising an osteogenic material packed within said cavity.

13. The method of claim 12 wherein the osteogenic material is packed within the cavity prior to implantation of the graft.

14. The method of claim 12 wherein the osteogenic material is packed within the cavity after implantation of the graft.

15. The method of claim 4 comprising placing osteogenic material in the space around the graft.

16. The method of claim 4 comprising threadingly implanting the graft in to the space.

17. The method of claim 16 wherein the graft includes a tool engagement end having an alignment mark and wherein said threadingly implanting comprises orientating the alignment mark to facilitate placement of the graft in the space as desired.

18. The method of claim 16 comprising implanting a second graft into the space.

19. The method of claim 18 wherein the second graft includes a tool engagement having an alignment mark and wherein said implanting a second graft comprises orientating the alignment mark of the second graft to facilitate placement of the second graft in the space as desired.

20. The method of claim 4 wherein said implanting comprises impacting the graft into the space.

21. The method of claim 4 comprising implanting a second graft into the space.

22. The method of claim 4, wherein the graft includes a tool engagement end and said implanting comprises attaching an insertion tool having a shaft to the engagement end of the graft.

23. The method of claim 22 wherein the shaft is threaded and said attaching comprising threadedly engaging the shaft with the graft.

24. The method of claim 4 wherein the graft includes a tool engagement end and said implanting comprises attaching an insertion tool to the engagement end of the graft, said insertion tool comprising an occlusion member configured to overlay at least a portion of the chamber.

25. The method of claim 24 comprising packing the chamber with an osteogenic material and extending the occlusion member to overlay at least a portion of the chamber.

26. The method of claim 4 wherein the graft includes a channel extending from the tool engagement end to the chamber, and said occlusion member is configured to be slidable received within the channel.

27. The method of claim 22 wherein the insertion tool includes an extendable shaft to engage with the engagement end of the graft.

28. The method of claim 4 wherein the graft includes a tool engagement end and said implanting comprises attaching an insertion tool having a pair of prongs configured to engage the outer surface of the graft.

29. The method of claim 28 wherein the insertion tool includes an extendable shaft to engage with the engagement end of the graft.

30. A method for fusing two adjacent vertebrae, said method comprising:
   preparing a disc space between the two adjacent vertebrae to receive a spacer
   providing a spacer comprising a C-shaped body formed of cortical bone, said body comprising a cavity having a concave surface; and
   implanting the spacer in the space between the two adjacent vertebrae.

31. The method of claim 30 comprising inserting an osteogenic material into the cavity.

32. The method of claim 31 wherein the osteogenic material is inserted into the cavity prior to implantation of the spacer into the disc space.

33. The method of claim 31 wherein the osteogenic material is inserted into the cavity after to implantation of the spacer into the disc space.

34. The method of claim 30 comprising threadingly implanting the spacer in to the disc space.

35. The method of claim 34 wherein the spacer comprises vertebrae engaging surfaces including on of ribs, grooves and threads.

36. The method of claim 30 comprising impacting the spacer into the disc space.

37. The method of claim 36 wherein the spacer is provided as a dowel having a substantially round cross sectional area when viewed adjacent a first end.

38. The method of claim 36 wherein the spacer is provided with flattened upper and lower surfaces.

39. The method of claim 30 wherein the spacer comprises vertebrae engaging surfaces including on of ribs, grooves and threads.

40. The method of claim 30 wherein the spacer includes a tool engagement end having an alignment mark and wherein said implanting comprises orientating the alignment mark to facilitate placement of the spacer in the disc space as desired.

41. The method of claim 30 comprising implanting a second spacer into the disc space.

42. The method of claim 41 wherein the second spacer includes a tool engagement end having an alignment mark and wherein said implanting a second spacer comprises orientating the alignment mark of the second spacer to facilitate placement of the spacer in the disc space as desired.

43. The method of claim 42 wherein said orientating the alignment mark of the second spacer comprising orientating the second spacer relative to the first spacer so that the cavity of the first spacer and the cavity of the second spacer oppose each other in the disc space.

44. The method of claim 30 wherein the spacer includes a tool engagement end and said implanting comprises attaching an insertion tool having an extendable shaft to the engagement end of the spacer.

45. The method of claim 30 wherein the spacer includes a tool engagement end and said implanting comprises attaching an insertion tool to the engagement end of the spacer, said insertion tool comprising an occlusion member configured to extend to overlay at least a portion of the chamber.

46. The method of claim 30 wherein the spacer includes a tool engagement end and said implanting comprises attaching an insertion tool having a pair of prongs configured to engage the C-shaped body.

* * * * *